(12) United States Patent
Nagasawa

(10) Patent No.: US 7,586,610 B2
(45) Date of Patent: Sep. 8, 2009

(54) COMPONENT MEASURING DEVICE

(75) Inventor: Yasushi Nagasawa, Ymanashi-ken (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 436 days.

(21) Appl. No.: 10/557,782

(22) PCT Filed: May 21, 2004

(86) PCT No.: PCT/JP2004/007305

§ 371 (c)(1),
(2), (4) Date: Nov. 18, 2005

(87) PCT Pub. No.: WO2004/111622

PCT Pub. Date: Dec. 23, 2004

(65) Prior Publication Data

US 2006/0243031 A1 Nov. 2, 2006

(30) Foreign Application Priority Data

| May 21, 2003 | (JP) | ............................. 2003-144131 |
| Jul. 25, 2003 | (JP) | ............................. 2003-201933 |
| Sep. 19, 2003 | (JP) | ............................. 2003-328879 |

(51) Int. Cl.
G01N 21/25 (2006.01)
(52) U.S. Cl. ......................................... 356/402; 356/39
(58) Field of Classification Search ................. 356/213, 356/39, 402
See application file for complete search history.

(56) References Cited

U.S. PATENT DOCUMENTS 3,699,383 A * 10/1972 Chaney ....................... 356/314
4,959,547 A * 9/1990 Carroll et al. ............ 250/336.1

(Continued)

FOREIGN PATENT DOCUMENTS

JP 62-12856 A 1/1987

(Continued)

OTHER PUBLICATIONS

English language Translation of Official Action issued in Japanese Patent Application No. 2003-201933 on May 15, 2008.

(Continued)

Primary Examiner—Kara E Geisel
(74) Attorney, Agent, or Firm—Buchanan Ingersoll & Rooney PC

(57) ABSTRACT

A component measuring device for measuring the quantity and/or the property of a given component in a specimen by calorimetrically measuring a test strip includes a tip mount on which is to be mounted a tip having the test strip, and a photometric unit. The photometric unit comprises a light-emitting element that applies light to the test strip while the tip is mounted on the tip mount, a light-detecting element that detects light reflected from the test strip, and a holder in which is held the light-emitting element and the light-detecting element. The holder possesses a passage through which passes the light and the reflected light. A light-transmissive member closes the passage with a sealing member interposed therebetween in a portion of the holder which faces the test strip. The component measuring device can also be provided with a stain detecting device which is adapted to detect a stain on the light-transmissive member.

19 Claims, 20 Drawing Sheets

U.S. PATENT DOCUMENTS

| | | | |
|---|---|---|---|
| 5,037,614 A * | 8/1991 | Makita et al. | 422/68.1 |
| 5,208,147 A * | 5/1993 | Kagenow et al. | 435/14 |
| 5,597,532 A * | 1/1997 | Connolly | 422/58 |
| 5,736,103 A | 4/1998 | Pubh | |
| 5,772,606 A * | 6/1998 | Ashibe et al. | 600/573 |
| 6,055,050 A * | 4/2000 | Skiffington | 356/244 |
| 6,083,460 A | 7/2000 | Morikawa et al. | |
| 6,099,484 A * | 8/2000 | Douglas et al. | 600/583 |
| 6,335,203 B1 * | 1/2002 | Patel et al. | 436/169 |
| 6,338,720 B1 | 1/2002 | Morikawa et al. | |
| 6,491,870 B2 * | 12/2002 | Patel et al. | 422/58 |
| 6,574,425 B1 * | 6/2003 | Weiss et al. | 356/402 |
| 6,952,263 B2 * | 10/2005 | Weiss et al. | 356/425 |
| 6,958,129 B2 * | 10/2005 | Galen et al. | 422/57 |
| 7,262,061 B2 * | 8/2007 | Petrich et al. | 436/169 |
| 2006/0024203 A1 * | 2/2006 | Jansen et al. | 422/82.05 |
| 2006/0222567 A1 * | 10/2006 | Kloepfer et al. | 422/68.1 |

FOREIGN PATENT DOCUMENTS

| | | |
|---|---|---|
| JP | 3-46524 A | 2/1991 |
| JP | 3-95431 A | 4/1991 |
| JP | 3-95438 A | 4/1991 |
| JP | 3-95439 A | 4/1991 |
| JP | 3-95440 A | 4/1991 |
| JP | 3-52635 | 5/1991 |
| JP | 3-52635 U | 5/1991 |
| JP | 5-142046 A | 6/1993 |
| JP | 6-288916 A | 10/1994 |
| JP | 8-15142 A | 1/1996 |
| JP | 8-36124 A | 2/1996 |
| JP | 10-82733 A | 3/1998 |
| JP | 10-148635 A | 6/1998 |
| JP | 10-318928 A | 12/1998 |
| JP | 10-329653 A | 12/1998 |
| JP | 11-183474 A | 7/1999 |
| JP | 2000-230904 A | 8/2000 |
| JP | 2000-230905 A | 8/2000 |
| JP | 2002-196075 A | 7/2002 |

OTHER PUBLICATIONS

English language Translation of Official Action issued in Japanese Patent Application No. 2003-144131 on May 15, 2008.

English language Translation of Official Action issued in Japanese Patent Application No. 2003-328879 on May 15, 2008.

* cited by examiner

COMPONENT MEASURING DEVICE

This application is the U.S. national stage application of International Application No. PCT/JP2004/007305 filed on May 21, 2004 designating the United States, the entire content of which is incorporated herein by reference. This application is also based on and claims priority under 35 U.S.C. § 119(a) to Japanese Application No. 2003-144131 filed on May 21, 2003, Japanese Application No. 2003-201933 filed on Jul. 25, 2003 and Japanese Application No. 2003-328879 filed on Sep. 19, 2003, the entire content of each of which is incorporated herein by reference.

TECHNICAL FIELD

The present invention relates to a component measuring device for measuring the quantity and/or the property of a component in question, such as for measuring a blood glucose level.

BACKGROUND ART

There is known a blood glucose level measuring device (blood component measuring device) for measuring a blood glucose level. The blood glucose level measuring device quantifies a blood glucose level by optically measuring (calorimetrically measuring) a color that is developed by a test strip depending on the amount of glucose in blood.

The conventional blood glucose level measuring device includes a photometric unit having a light-emitting element and a light-detecting element. The photometric unit measures the color of the test strip by applying light to the test strip and measuring the intensity of reflected light.

The photometric unit has a passage for passing therethrough the light to be applied to the test strip and the reflected light from the test strip. The passage is open in a portion of the photometric unit which faces the test strip.

The photometric unit of the above component measuring device suffers a problem in that dust or foreign matter tends to be trapped in the photometric unit. The problem has heretofore been addressed by Japanese Patent Laid-Open No. Hei 3-95438 and Japanese Patent Laid-Open No. Hei 3-95439.

Japanese Patent Laid-Open No. Hei 3-95431 and Japanese Patent Laid-Open No. Hei 3-95440 have proposed placing a transparent plate on the front surface of a photometric unit to prevent dust from entering the component measuring device.

With the conventional blood glucose level measuring device, however, since the opening is not sealed in a liquid-tight manner, blood applied to the test strip may be trapped into the passage in the photometric unit, and it is difficult to remove the trapped blood from the test strip.

Furthermore, if a liquid such as water and an aqueous solution of ethanol is used to wash away a stain such as dust, blood, urine, and fingerprint, then the liquid may possibly enter the blood glucose level measuring device.

If foreign matter such as water and blood is introduced into the passage in the photometric unit, then the measured value of the blood glucose level varies, resulting in a reduction in the measurement accuracy.

Stains such as dust, dirt, fingerprint and blood may be applied to the transparent plate. The applied stains are liable to cause the measured value of the blood glucose level to vary, resulting in a reduction in the measurement accuracy. Therefore, stains on the transparent plate need to be detected.

Heretofore, it has been customary to detect such stains according to a white level checking process. According to the white level checking process, a white pattern is placed at the tip end of the photometric unit, and when a stain is applied to the transparent plate, the sum of the amount of reflected light from the white pattern and the amount of reflected light from the transparent plate is reduced.

More specifically, a stain is detected by the white level checking process as follows: A tip having a test strip (white) is mounted on the photometric unit. The tip is irradiated with light emitted from the light-emitting element of the photometric unit, and reflected light reflected from the tip is detected by the light-detecting element. A stain on the transparent plate is detected based on the amount of light detected by the light-detecting element. If the amount of light detected by the light-detecting element is smaller than a predetermined threshold, then it is determined that the transparent plate is stained.

According to the white level checking process for detecting a stain, however, the strong reflected light from the test strip and the weak reflected light from the stain on the transparent plate are mixed with each other, tending to fail to detect a stain on the transparent plate highly accurately.

DISCLOSURE OF INVENTION

It is an object of the present invention to provide a component measuring device having high measurement accuracy.

Another object of the present invention is to provide a component measuring device having high measurement accuracy, which is capable of accurately detecting a stain on a light-transmissive member.

To achieve the above objects, there is provided in accordance with the present invention a component measuring device for measuring a quantity and/or a property of a given component in a specimen by calorimetrically measuring a test strip, including: a tip mount for removably mounting a tip having the test strip; and a photometric unit having a light-emitting element for applying light to the test strip while the tip is being mounted on the tip mount, a light-detecting element for detecting reflected light reflected from the test strip, and a holder for accommodating and holding the light-emitting element and the light-detecting element. The holder has a passage for passing the light and the reflected light therethrough, and a light-transmissive member is disposed to close the passage with a sealing member interposed therebetween in a portion of the holder which faces the test strip.

With this arrangement, dust, blood (specimen), or the like is reliably prevented from entering into the passage in the photometric unit (into the photometric unit). Even if dust, the specimen, or the like is applied to an end of the photometric unit or the like, it can easily and reliably be removed. Therefore, the amount of a blood component in question can be measured with high measurement accuracy.

There is also provided in accordance with the present invention a component measuring device for measuring a quantity and/or a property of a given component in a specimen by calorimetrically measuring a test strip, including: a tip mount for removably mounting a tip having the test strip; and a photometric unit having a light-emitting element for applying light to the test strip while the tip is being mounted on the tip mount, a light-detecting element for detecting reflected light reflected from the test strip, and a holder for accommodating and holding the light-emitting element and the light-detecting element. The holder has a passage for passing the light and the reflected light therethrough, and a light-transmissive member is fixed to the holder by a holder member in a portion of the holder which faces the test strip, and is disposed to close the passage with a sealing member interposed therebetween.

With this arrangement, dust, blood (specimen), or the like is reliably prevented from entering into the passage in the photometric unit (into the photometric unit). Even if dust, the specimen, or the like is applied to an end of the photometric unit or the like, it can easily and reliably be removed. Therefore, the amount of a blood component in question can be measured with high measurement accuracy.

In the component measuring device according to the present invention, the light-transmissive member preferably isolates the test strip and the passage of the holder from each other with the tip being mounted on the tip mount.

In the component measuring device according to the present invention, the light-transmissive member preferably includes a flat plate and has a surface facing the test strip and lying substantially flush with an end face of the holder.

In the component measuring device according to the present invention, the sealing member is preferably made of an elastomeric material.

In the component measuring device according to the present invention, the tip mount is preferably disposed at an end of the photometric unit where the passage is open.

In the component measuring device according to the present invention, the holder member preferably has an abutment portion held in abutment against the light-transmissive member, the abutment portion having an opening for passing the light and the reflected light therethrough.

In the component measuring device according to the present invention, the opening preferably has a cross-sectional area which is substantially constant from an outer end thereof to an inner end thereof.

In the component measuring device according to the present invention, the opening preferably has a cross-sectional area which is progressively reduced from an outer end thereof to an inner end thereof.

In the component measuring device according to the present invention, the opening preferably has a cross-sectional area (average) ranging from 0.1 to 100 mm$^2$.

In the component measuring device according to the present invention, the opening preferably has a cross-sectional shape which is substantially equal from an outer end thereof to an inner end thereof.

In the component measuring device according to the present invention, if it is assumed that the maximum spaced distance between opposite inner surfaces of the opening in the vertical cross section is represented by $L_1$ [mm] and the thickness of the opening by $L_2$ [mm], then the ratio $L_2/L_1$ should preferably satisfy the relationship indicated by 0.1 or greater.

In the component measuring device according to the present invention, the abutment portion preferably includes a flat plate having a thickness (average) ranging from 0.1 to 10 mm.

In the component measuring device according to the present invention, the opening area of the inner end of the opening should preferably be greater than the opening area of the passage of the holder.

There is also provided in accordance with the present invention a component measuring device for measuring a quantity and/or a property of a given component in a specimen by calorimetrically measuring a test member, including: a tip mount for removably mounting a tip having the test member; a photometric unit having a light-emitting element for applying light to the test member of the tip for measurement, a light-detecting element for detecting reflected light reflected from the test member, and a holder for accommodating and holding the light-emitting element and the light-detecting element; a light-shielding test tip for being removably mounted on the tip mount, wherein the holder has a passage for passing the light and the reflected light therethrough, and a light-transmissive member is disposed in a portion of the holder which faces the test member; and stain detecting means for detecting a stain on the light-transmissive member based on an amount of light detected by the light-detecting element when light is emitted from the light-emitting element of the photometric unit and light is detected by the light-detecting element while the test tip is being mounted on the tip mount, wherein the stain detecting means is arranged to determine that there is a stain on the light-transmissive member if the amount of light detected by the light-detecting element is greater than a threshold in detecting a stain on the light-transmissive member.

With this arrangement, a stain on the light-transmissive member can be detected with high accuracy. Since an amount of a blood component in question is prevented from being measured while the light-transmissive member is being stained, the measurement accuracy is increased. Since the component measuring device has the light-transmissive member, dust, the specimen, or the like is reliably prevented from entering into the passage in the photometric unit (into the photometric unit), so that an amount of a blood component in question can be measured with high measurement accuracy.

In the component measuring device according to the present invention, the test tip preferably has a lid-like member for covering a distal end of the tip mount.

In the component measuring device according to the present invention, at least the lid-like member of the test tip is preferably black or dark in color.

In the component measuring device according to the present invention, the distance from the distal end of the tip mount to an inner wall of the lid-like member at a distal end thereof is preferably 10 mm or greater while the test tip is being mounted on the tip mount.

There is also provided in accordance with the present invention a component measuring device for measuring a quantity and/or a property of a given component in a specimen by calorimetrically measuring a test member, including: a tip mount for removably mounting a tip having the test member; a photometric unit having a light-emitting element for applying light to the test member of the tip for measurement, a light-detecting element for detecting reflected light reflected from the test member, and a holder for accommodating and holding the light-emitting element and the light-detecting element, wherein the holder has a passage for passing the light and the reflected light therethrough, and a light-transmissive member is disposed in a portion of the holder which faces the test member; and stain detecting means for detecting a stain on the light-transmissive member based on an amount of light detected by the light-detecting element when light is emitted from the light-emitting element of the photometric unit and light is detected by the light-detecting element, wherein the stain detecting means is arranged to determine that there is a stain on the light-transmissive member if the amount of light detected by the light-detecting element is greater than a threshold in detecting a stain on the light-transmissive member.

With this arrangement, a stain on the light-transmissive member can be detected with high accuracy. Since an amount of a blood component in question is prevented from being measured while the light-transmissive member is being stained, the measurement accuracy is increased. Since the component measuring device has the light-transmissive member, dust, the specimen, or the like is reliably prevented from entering into the passage in the photometric unit (into the photometric unit), so that an amount of a blood component in question can be measured with high measurement accuracy.

In the component measuring device according to the present invention, a stain on the light-transmissive member is preferably detected while the tip is not being mounted on the tip mount.

In the component measuring device according to the present invention, a stain on the light-transmissive member is preferably detected when a power supply of the component measuring device is turned on.

The component measuring device according to the present invention preferably has a stain detecting mode for detecting a stain on the light-transmissive member.

The component measuring device according to the present invention preferably further includes storage means. A stain on the light-transmissive member is preferably detected after measurement, and a detected result is preferably stored in the storage means.

In the component measuring device according to the present invention, when a stain on the light-transmissive member is not detected, information stored in the storage means is used.

In the component measuring device according to the present invention, when the component measuring device is powered on with the tip being mounted on the tip mount, a stain on the light-transmissive member is not detected and information stored in the storage means is used.

The component measuring device according to the present invention preferably further includes: indicating means for indicating a detected result produced in detecting a stain on the light-transmissive member.

In the component measuring device according to the present invention, the light-transmissive member is preferably disposed to close the passage with a sealing member interposed therebetween.

BEST MODE FOR CARRYING OUT THE INVENTION

Component measuring devices according to the present invention will be described in detail below with respect to preferred embodiments illustrated in the accompanying drawings. Prior to describing embodiments of component measuring devices according to the present invention, an embodiment of a tip (component measuring tip) for use on the component measuring devices according to the present invention will first be described below.

Figure 7:
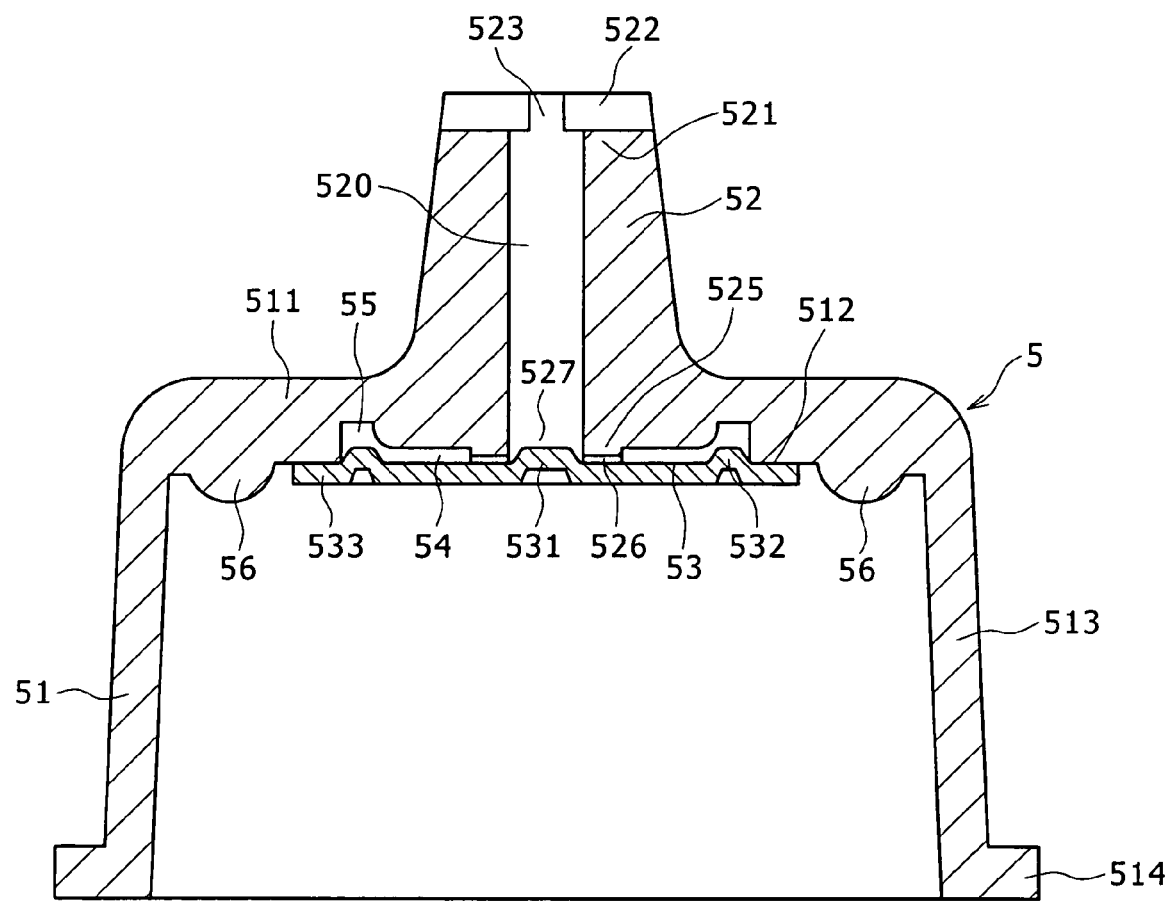
FIG. 7 is a vertical cross-sectional view of a tip.
Figure 8:
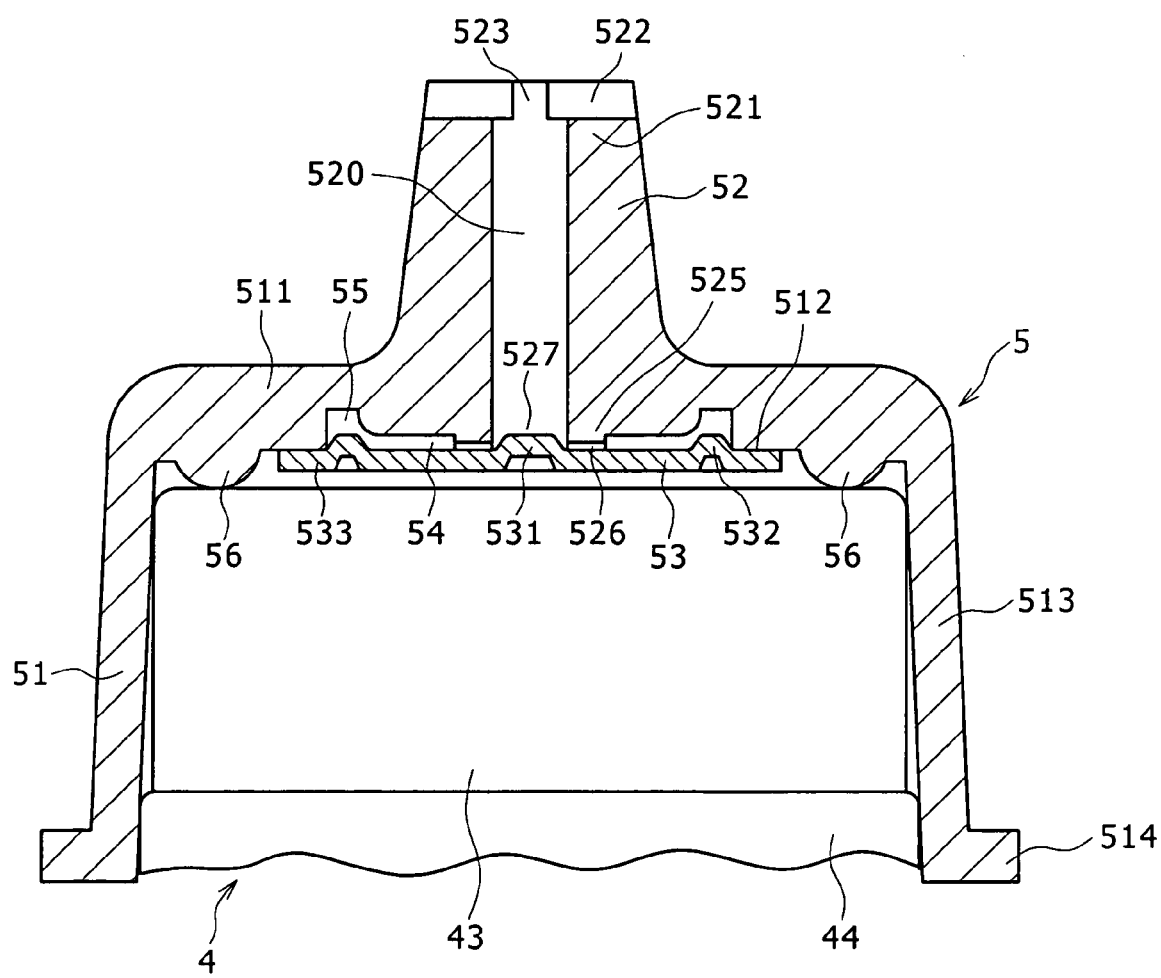
FIG. 8 is a vertical cross-sectional view of the tip shown in FIG. 7 which is mounted on the component measuring device.

FIG. 7 is a vertical cross-sectional view of a tip, and FIG. 8 is a vertical cross-sectional view of the tip shown in FIG. 7 which is mounted on the component measuring device. The lower side in FIGS. 7 and 8 will be referred to as "proximal end" and the upper side as "distal end".

A tip 5 shown in FIG. 7 includes a bottomed tubular tip body 51, a thin tube 52 projecting from a bottom 511 of the tip body 51, and a test strip 53 as a test member disposed in the tip body 51.

The tip body 51 serves as a mount for supporting the test strip 53 and mounting the tip 5 on a distal end (tip mount) of a photometric unit 4 of a component measuring device 1 to be described later.

The tip body 51 includes the bottom 511, a barrel 513, and a flange 514 disposed on the outer circumferential surface of the proximal end of the barrel 513. A seat 512 for fixing the test strip 53 thereto is disposed on an inner surface of the bottom 511. The test strip 53 has an outer circumferential edge (fixed portion 533) fixed to the seat 512 by fusion bonding, adhesive bonding, or the like.

Figure 9:
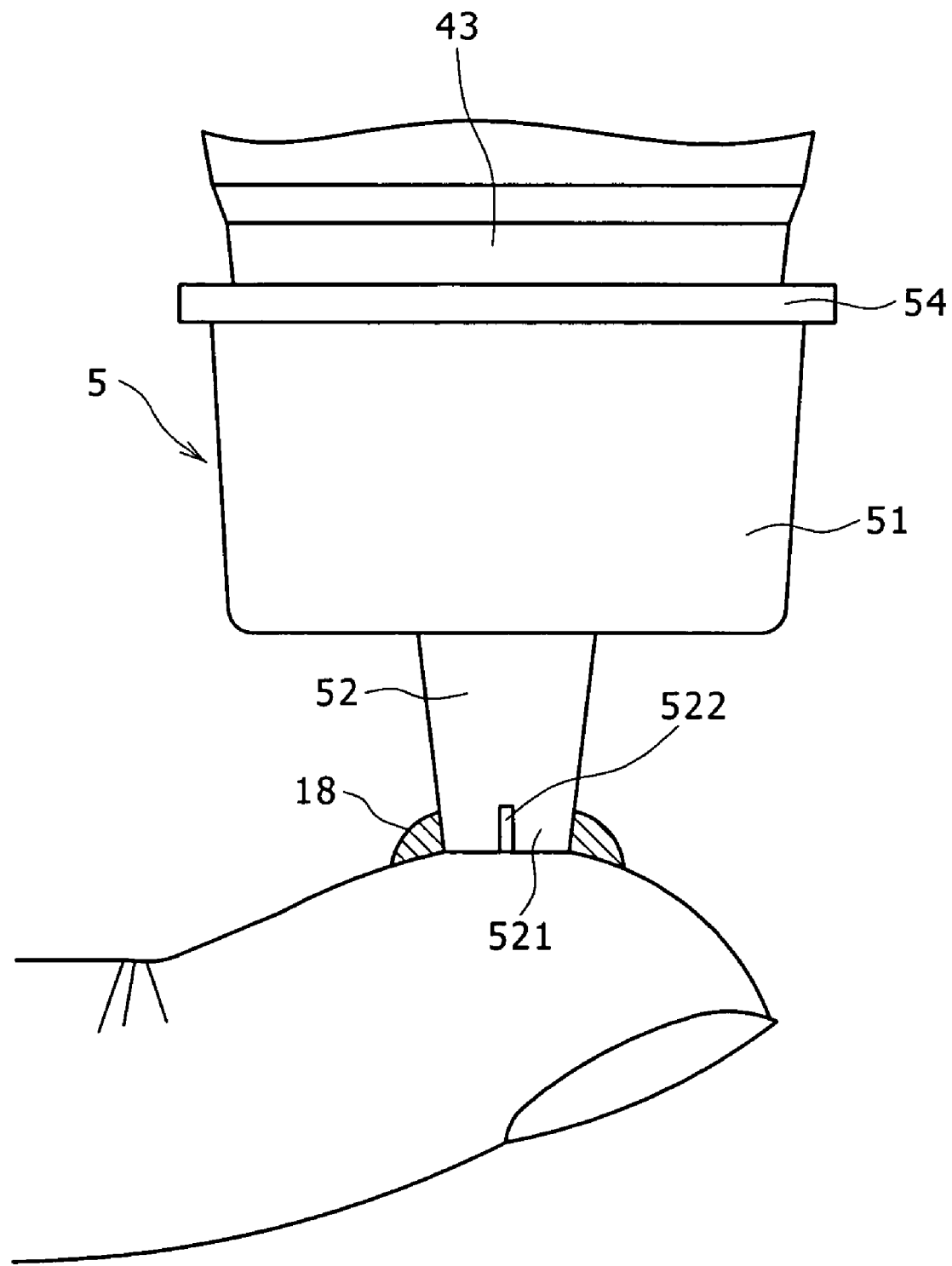
FIG. 9 is a side elevational view showing the manner in which a blood is sampled using the tip shown in FIG. 7.

The barrel 513 serves as a mount for mounting the tip 5 on the tip end of the photometric unit 4 of the component measuring device 1. Specifically, as shown in FIGS. 8 and 9, the tip end of the photometric unit 4 (holder 43) is fitted in the barrel 513 of the tip body 51, thereby mounting the tip 5 on the photometric unit 4 of the component measuring device 1. The state shown in FIG. 8 will hereinafter referred to as "tip mounted state".

The thin tube 52, which serves to sample a blood (specimen), has a specimen introduction passage 520 defined therein. The specimen introduction passage 520 extends in a direction substantially perpendicular to the test strip 53, and has a specimen inlet port 523 in the distal end thereof and a specimen outlet port 527 in the proximal end thereof.

Since the blood is supplied through specimen introduction passage 520 due to a capillary action to the test strip 53, the inside diameter (average) of the specimen introduction passage 520 should preferably be in the range from about 0.2 to 2.0 mm, and more preferably be in the range from about 0.3 to 1.0 mm. If the inside diameter of the specimen introduction passage 520 is too large, then it is difficult to deliver the blood by way of a capillary action, and if the inside diameter is too small, then the blood is supplied at a low rate and it takes a long period of time to supply a sufficient amount of blood to the test strip 53.

The inside diameter (cross-sectional area) of the specimen introduction passage 520 may be constant or vary along the longitudinal direction of the specimen introduction passage 520.

The length (entire length) of the specimen introduction passage 520 should preferably be in the range from about 1 to 10 mm, and more preferably be in the range from about 2 to 5 mm. If the length of the specimen introduction passage 520 is too large, then it takes long time to deliver the blood by way of a capillary action, and if the length is too small, then the blood 18 may possibly be applied to the outer surface of the bottom of the tip body 51 in the state shown in FIG. 9.

As shown in FIG. 7, the distal end and the proximal end of the thin tube 52 provide a specimen inlet end 521 and a specimen outlet end 525, respectively.

A groove 522 is defined in the end face of the specimen inlet end 521 in communication with the specimen introduction passage 520. In the illustrated structure, the groove 522 is a straight groove extending diametrically across the thin tube 52. The groove 522 has opposite ends that are open at the outer circumferential surface of the thin tube 52.

The specimen outlet end 525 (near the test strip 53) of the thin tube 52 is formed as a land slightly projecting into the tip body (toward the proximal end). The end face of the specimen outlet end 525 has a groove (second groove) 526 communicating with the specimen introduction passage 520. In the illustrated structure, the groove 526 is a straight groove extending diametrically across the thin tube 52. The groove 526 has opposite ends that are open at the outer circumferential surface of the projecting portion (the thin tube 52).

As shown in FIG. 7, a gap 54 is present on the side of the test strip 53 near the thin tube 52, i.e., between the test strip 53 and the inner surface of the bottom 511 of the tip body 51. The gap 54 has a function to assist in spreading the blood on the test strip 53.

A specimen reservoir 55 in the form of an annular recess held in communication with the gap 54 and deeper than the gap 54 is disposed in an outer circumferential area of the gap 54. The blood that has been spread radially through the gap 54 is trapped in the specimen reservoir 55 and prevented from moving radially outwardly (into the region of the test strip 53 that is fixed by adhesive bonding, fusing, or the like). Therefore, even if the blood is supplied excessively, the excessive blood is prevented from leaking out. Thus, the photometric unit 4 of the component measuring device 1 is prevented from being contaminated by blood deposits.

A spacer 56 is disposed radially outwardly of the seat 512 on the inner surface of the bottom 511 of the tip body 51. The spacer 56 serves as spacing means for keeping the test strip 53 and the holder 43 out of contact with each other when the tip 5 is mounted in place.

The spacer 56 includes a plurality of (e.g., four at angular intervals of 90°) protrusions arrayed circumferentially on the inner surface of the bottom 511. As shown in FIG. 8, the spacer 56 abuts against the tip end of the holder 43 of the photometric unit 4 to prevent the tip end of the holder 43 from contacting the test strip 53.

The spacer 56 thus protects the test strip 53 and prevents the blood spread in the test strip 53 from being applied to and contaminating the photometric unit 4.

The spacer 56 also has a function to abut against the tip end of the holder 43 to keep the test strip 53 and a light-emitting element 41 and a light-detecting element 42 of the photometric unit 4 spaced from each other by a constant distance. Therefore, a measurement error which would otherwise be caused if the distance changed to vary the optical characteristics is minimized for increased measurement accuracy.

The tip 5 is not limited to the structure having the flange 514 and the thin tube 52, but may be in the form of a flat plate, a sheet, or a stick, for example.

The tip body 51 and the thin tube 52 are made of a rigid material having a predetermined rigidity. The rigid material may be any of various resin materials including acrylic resin, polystyrene, polyethylene, polypropylene, hard polyvinyl chloride, polycarbonate, polymethyl methacrylate, ABS resin, polyester, polyphenylene sulfide (PPS), polyamide, polyimide, and polyacetal, or a polymer alloy, and a polymer blend which contains one or more of the above resin materials. Of these materials, highly hydrophilic materials such as acrylic resin or materials that have been hydrophilicized are particularly suitable for quickly introducing and spreading the specimen.

The hydrophilicizing process may be a physically activating process such as plasma processing, glow discharge, corona discharge, and ultraviolet irradiation, or the addition (coating) of a surface active agent, water-soluble silicone, hydroxypropyl cellulose, polyethylene glycol, polypropylene glycol, or the like.

The test strip 53 includes a carrier capable of absorbing the blood (specimen), the carrier carrying (being impregnated with) a reagent (coloring reagent). The carrier should preferably include a porous film (sheet-like porous base). The porous film should preferably have a pore diameter small enough to filtrate red cells in the blood.

If the carrier in the form of a porous film is impregnated with a reagent that reacts with oxygen as a substrate such as in an oxidasic reaction, then even when the blood is spread in the test strip 53 and covers the blood reception side thereof, oxygen in the atmosphere is supplied from the reaction side (opposite side) to keep the reaction in rapid progress for allowing a colored state to be detected without removal of the blood.

The carrier of the test strip 53 may be a sheet-like porous base such as a non-woven fabric, a woven fabric, an oriented sheet, or the like, other than a porous film.

The carrier such as a porous film may be made of any of various polyesters, polyamides, polyolefins, polysulfons, celluloses, or the like. However, because the carrier needs to be impregnated with an aqueous solution with a reagent dissolved therein and also needs to quickly absorb and spread blood when blood is sampled, the carrier should preferably be made of a hydrophilic material or a hydrophilicized material. The hydrophilicizing process may be the same as those described above.

The reagent used to impregnate the carrier (porous film) may be glucose oxidase (GOD), peroxidase (POD), or a coloring agent (coloring reagent) such as 4-aminoantipyrine or N-ethylN-(2-hydroxy-3-sulfopropyl)-m-toluidine for measuring a blood glucose level. Depending on a component to be measured, the reagent may be of a substance which reacts a component in question in blood (given component), such as ascorbate oxidase, alcohol oxidase, alcohol dehydrogenase, galactose oxidase, fructose dehydrogenase, cholesterol oxidase, cholesterol dehydrogenase, lactate oxidase, lactate dehydrogenase, bilirubin oxidase, and xanthin oxidase, or a coloring agent (coloring reagent) as described above. The reagent may contain a buffer such as a phosphoric acid buffer. However, the reagent is not limited to the types and components described above.

The shape and structure of the test strip 53 will be described below. The test strip 53 should preferably be of a circular shape. However, the shape of the test strip 53 is not limited to a circular shape, but may be selected where necessary from various shapes including an elliptical shape, a quadrangular shape such as a square shape, an elongate rectangular shape, a lozenge shape, or the like, a triangular shape, a hexagonal shape, and an octagonal shape.

The test strip 53 has an annular ridge 532 disposed radially inwardly (toward the center) from the outer circumferential edge (outermost edge) thereof and projecting in the same direction as a protrusion 531 thereof. The annular ridge 532 is of a circular shape around the protrusion 531 at its center and has a tip end inserted in the specimen reservoir 55.

The annular ridge 532 has a function to limit the blood from being spread in the test strip 53 for thereby preventing excessive blood from flowing radially outwardly beyond the annular ridge 532, thus preventing a contamination due to blood deposits.

Though the annular ridge 532 is not limited to any diameters, it should preferably have a diameter in the range from 75 to 95%, and preferably 85 to 95%, of the outside diameter of the test strip 53.

The annular ridge 532 should preferably have a width in the range from about 0.03 to 1.0 mm, and more preferably in the range from about 0.05 to 0.5 mm. The annular ridge 532 should preferably have a height in the range from about 0.02 to 1.0 mm, and more preferably in the range from about 0.05 to 0.4 mm.

The shape and dimensions (diameter, width, height, etc.) of the annular ridge 532 may be selected depending on the shape, etc. of the tip body 51.

As shown in FIG. 7, the test strip 53 has a fixed portion 533 positioned in its outer peripheral edge area, i.e., radially outwardly of the annular ridge 532. The fixed portion 533 is fixed to the seat 512 of the tip body 51 by fusing, adhesive bonding, or the like.

The test strip 53 may be fixed to the end face of the specimen outlet end 525 by fusing, adhesive bonding, or the like. In this manner, the test strip 53 may be supported on and fixed to the tip body 51 more stably. Furthermore, the test strip 53 may be prevented from hindering the spreading of the blood due to a gap which would otherwise be developed if deformed (curved, strained, or undulated).

FIG. 9 is a side elevational view showing the manner in which a blood is sampled using the tip 5. As shown in FIG. 9, a blood is sampled by piercing a fingertip (or an earlobe) with a needle, a surgical knife, or the like, letting a small amount (e.g., about 1 to 6 μL) of blood 18 flow from the pierced region onto the skin.

The tip 5 is mounted on the distal end (tip mount) of the photometric unit 4 of the component measuring device 1, bringing the end face of the specimen inlet end 521 into contact with the skin. The blood 18 on the fingertip flows through the groove 522 into the specimen inlet port 523, and then flows through the specimen introduction passage 520 toward the proximal end under the suction of a capillary action until it reaches the specimen outlet port 527. At this time, since the blood 18 on the fingertip is effectively drawn in from side openings of the groove 522 (which are open at the outer circumferential surface of the thin tube 52), the blood 18 is not excessively scattered on the skin and hence suffers a reduced loss.

When the blood reaches the specimen outlet port 527, it is contacted and absorbed by the protrusion 531 of the test strip 53. A portion of the blood flows through the groove 526 into the gap 54. After having flowed into the gap 54, the blood is absorbed and spread in the adjacent test strip 53, and further spread radially outwardly. As the test strip 53 absorbs and spreads the blood particularly in the vicinity of the protrusion 531, a new suction force is developed in the specimen introduction passage 520 for continuously supplying the blood to the test strip 53.

When the spreading of the blood in the test strip 53 is completed, a component in question (e.g., glucose) in the blood reacts with the reagent carried by the test strip 53, producing a color depending on the amount of the component in question. The colored test strip 53 is photometrically measured to measure the intensity of the color for thereby determining the amount (blood glucose level) of the component in question in the blood.

Though a test strip has been described as a test member, the test member is not limited to a test strip, but may be anything insofar as it can change reflected light depending on the component in question.

A component measuring device according to the present invention will be described below with reference to preferred embodiments which are shown in the accompanying drawings.

First Embodiment

A first embodiment of a component measuring device according to the present invention will be described below.

Figure 1:
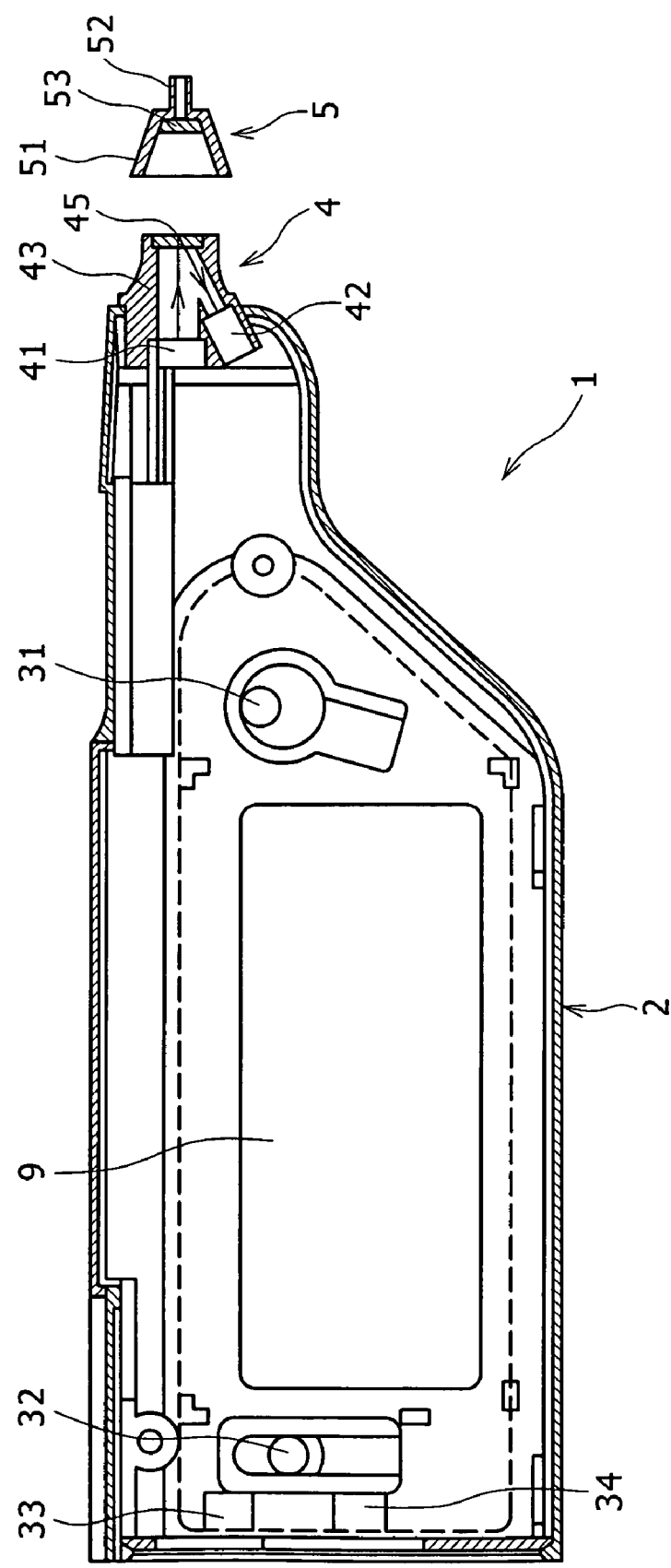
FIG. 1 is a plan view showing an internal structure of a first embodiment of a component measuring device according to the present invention.
Figure 2:
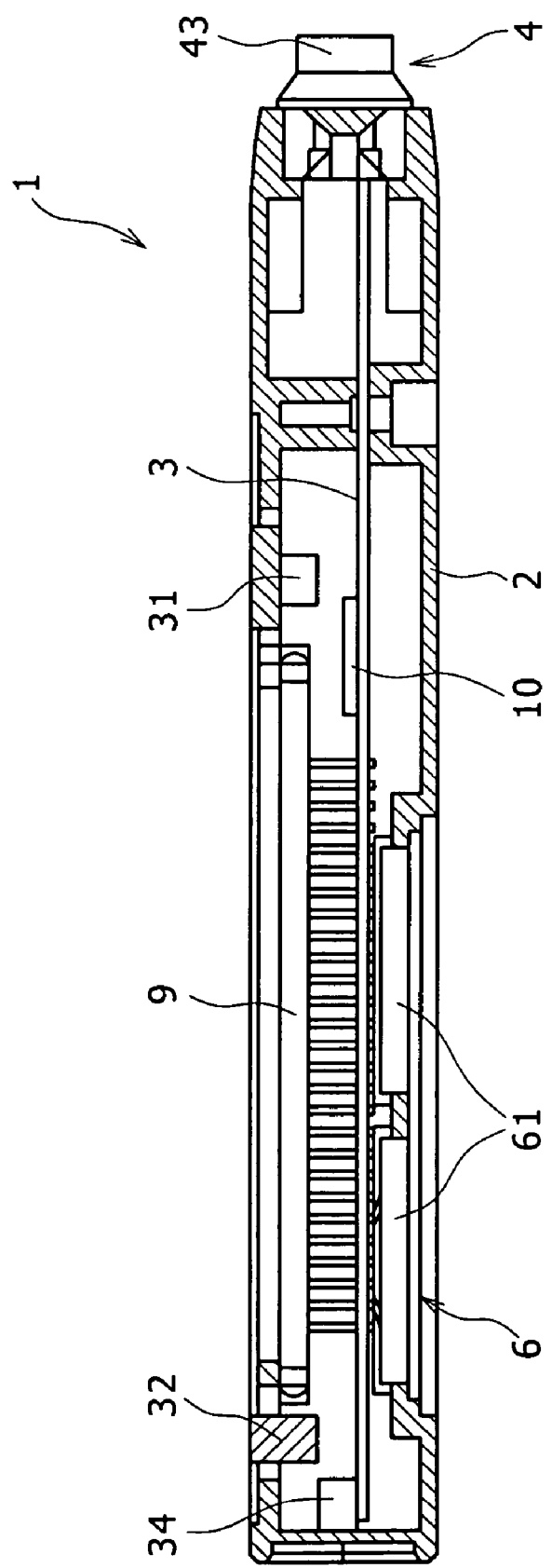
FIG. 2 is a sectional side elevational view of the component measuring device shown in FIG. 1.
Figure 3:
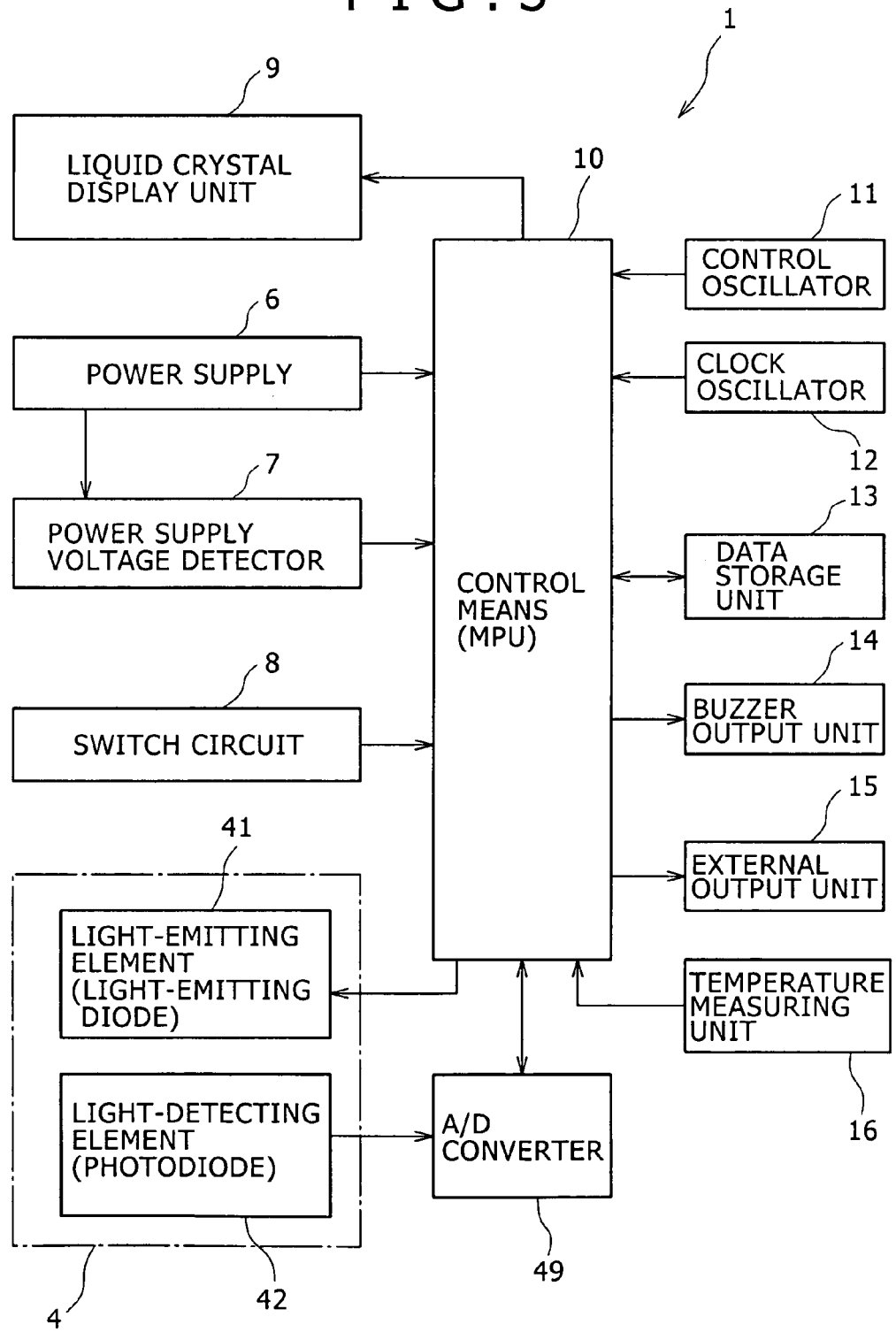
FIG. 3 is a block diagram of the component measuring device shown in FIG. 1.
Figure 4:
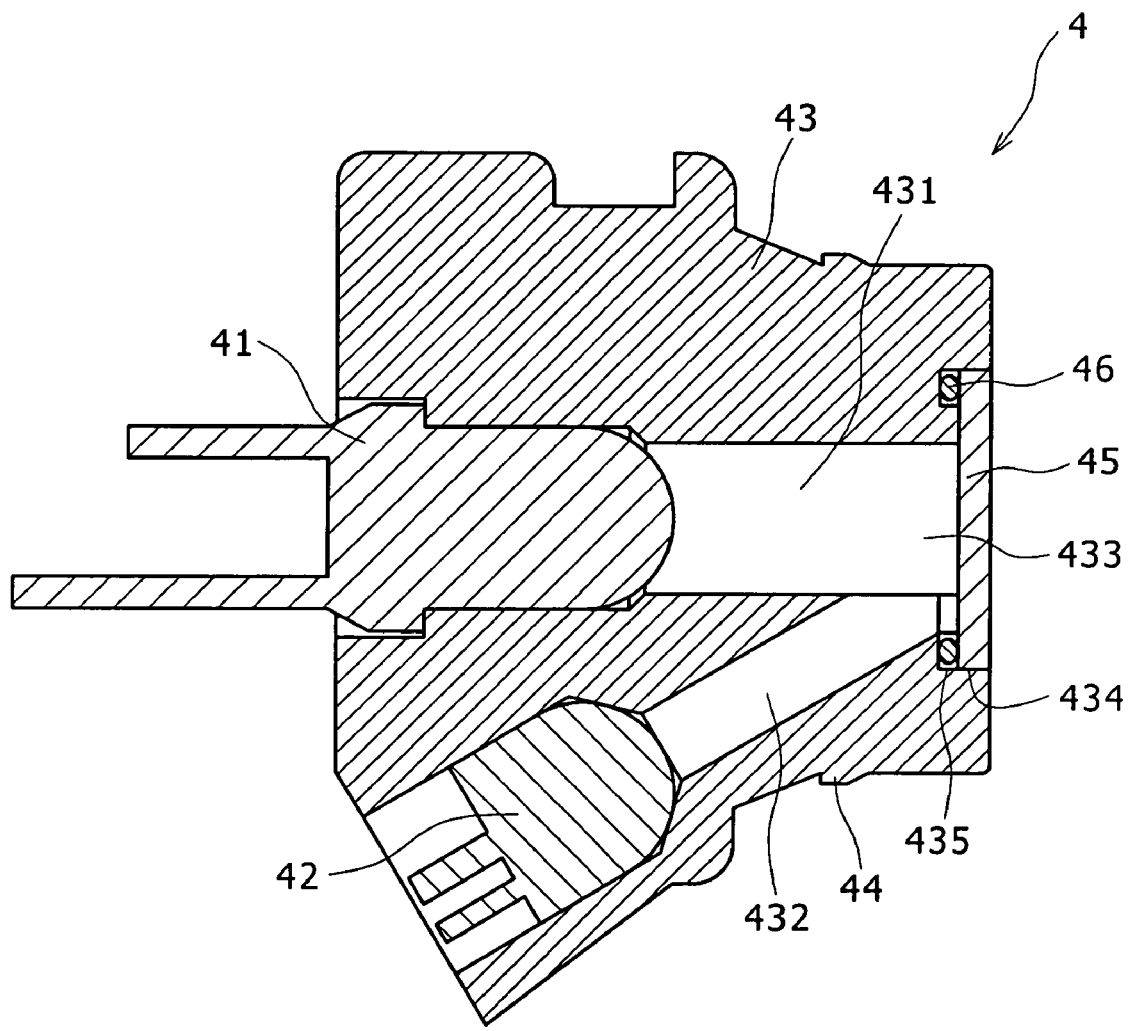
FIG. 4 is a vertical cross-sectional view of a photometric unit of the component measuring device shown in FIG. 1.

FIG. 1 is a plan view showing an internal structure of the first embodiment of the component measuring device according to the present invention, FIG. 2 is a sectional side elevational view of the component measuring device shown in FIG. 1, FIG. 3 is a block diagram of the component measuring device shown in FIG. 1, and FIG. 4 is a vertical cross-sectional view of a photometric unit of the component measuring device shown in FIG. 1. The left side in FIGS. 1, 2, and 4 will be referred to as "proximal end" and the right side as "distal end".

The component measuring device (blood component measuring device) 1 shown in these figures has a casing 2 in which a printed-circuit board 3 is disposed. A photometric unit 4 is disposed in the distal end of the casing 2. A liquid crystal display (LCD) unit 9 is installed in a window of the casing 2.

Control means 10 including a microcomputer is mounted on the printed-circuit board 3 for controlling various operations of the component measuring device 1. The control means 10 has a processor for calculating a blood component (e.g., glucose) in question based on a signal from the photometric unit 4. The processor also performs hematocrit value correcting calculations and temperature correcting calculations.

The photometric unit 4 has a light-emitting element (light-emitting diode) 41 and a light-detecting element (photodiode) 42 which are housed and held in a holder 43. The light-emitting element 41 is electrically connected to the control means 10, and the light-detecting element 42 is electrically connected to the control means 10 through an amplifier, not shown, and an A/D converter 49.

The light-emitting element 41 operates in response to a signal from the control means 10 to emit pulsed light at predetermined time intervals. The pulsed light has a period in the range from about 0.5 to 3.0 msec., for example, and the emission time of one pulse is in the range from about 0.05 to 0.3 msec.

The wavelength of the pulsed light should preferably be in the range from about 500 to 720 nm and more preferably in the range from about 580 to 650 nm.

A tip (component measurement tip) 5 incorporating therein a test strip 53 as described above is removably mounted on the distal end of the holder 43 (photometric unit 4). Specifically, a ring-shaped (annular) fitting portion 44 projects in a predetermined position from the distal end of the holder 43. When the tip 5 is mounted on the distal end of the holder 43 (tip mounted state), the proximal end of the tip body 51 is fitted in the fitting portion 44, fixing the tip 5 to the holder 43 (see FIG. 8). According to the present invention, therefore, the distal end of the holder 43 (the end of the photometric unit 4 where a first passage 431 and a second passage 432, described later, are open) serves as a tip mounting portion.

In the tip-mounted state, the distal end face of the holder 43 faces the test strip 53 in the tip 5. When the light-emitting element 41 is turned on, light emitted from the light-emitting element 41 is applied to the test strip 53, and reflected light reflected from the test strip 53 is detected by the light-detecting element 42, which photoelectrically converts the light into a signal. The light-detecting element 42 outputs an analog signal depending on the amount of detected light. The analog signal is amplified as desired, and then converted by the A/D converter 49 into a digital signal, which is applied to the control means 10.

The present invention resides in features of the photometric unit 4. These features will be described in detail later on.

The component measuring device 1 has a power supply 6, a power supply voltage detector 7, a switch circuit 8, a control oscillator 11, a clock oscillator 12, a data storage unit (storage means) 13, a buzzer output unit 14, an external output unit 15, and a temperature measuring unit 16.

Cells 61 are loaded in the power supply 6. The power supply voltage detector 7 detects the voltage of the cells 61, and outputs a detected voltage value (detected value) to the control means 10 for checking the remaining amount of electric energy in the cells 61.

The switch circuit 8 detects input signals from various switches described below, and applies the signals to the control means 10. The switches include a power supply switch, a stored data readout switch, a time setting/changing switch, a reset switch, a buzzer activation/inactivation selector switch, and a 50 Hz/60 Hz commercial power supply frequency selector switch.

The power supply switch can be turned on and off by pressing an operation button 31. The other switches can be actuated by operating either one or more of operating members 32, 33, 34 in combination.

The control oscillator 11 serves as a timer for generating clock pulses at certain time intervals, and supplies an operation reference signal for the microcomputer (microprocessing unit: MPU) of the control means 10.

The clock oscillator 12 serves as a clock for specifying absolute time (date and time). The clock oscillator 12 generates clock pulses at certain time intervals, and supplies an operation reference signal for a clock control circuit in the control means 10.

The data storage unit 13 has a first memory (RAM), a second memory (ROM), and a third memory (nonvolatile RAM) as a rewritable nonvolatile memory. Measured values (photometric data) input from the photometric unit 4 are stored according to a predetermined format in the first memory.

The second memory stores a table representative of the relationship (analytical curve) between absorbances determined from photometric values and amounts of a blood component in question.

The third memory stores in advance calibration values inherent to the individual device. The inherent calibration values include a rated value for amounts of reflected light and a corrective coefficient for absorbance calculations.

The buzzer output unit 14 energizes a buzzer to emit sound based on a signal from the control means 10.

The external output unit 15 serves to output data of a determined amount of a blood component in question to an external device such as a personal computer. The external output unit 15 has a communication driver such as RS232C. For performing infrared communications, the external output unit 15 has an infrared radiation emitter and a driver circuit therefor.

The temperature measuring unit 16 has a temperature sensor (thermistor) for measuring an ambient temperature. The temperature measuring unit 16 measures a temperature from time to time, and temperature information from the temperature measuring unit 16 is stored in the first memory of the data storage unit 13. Temperature information read from the first memory is input to the control means 10 for use in calculations for temperature-correcting an amount of a blood component in question.

The present invention resides in features of the structure of the photometric unit 4 described above. These points (features) will be described in detail below with reference to FIG. 4.

As described above, the photometric unit 4 has the holder (photometric block) 43 in which the light-emitting element 41 and the light-detecting element 42 are fixed in position. The holder 43 has a first passage 431 for passing and guiding light emitted from the light-emitting element 41 therethrough to the test strip 53, and a second passage 432 for passing and guiding reflected light reflected by the test strip 53 to the light-detecting element 42.

The first passage 431 and the second passage 432 are united together (join each other) in the distal end of the holder 43, and are open at the distal end of the holder 43. The distal end of the holder 43 has an opening 433 where the first passage 431 and the second passage 432 are open.

The opening 433 should preferably be of a circular shape. However, the shape of the opening 433 may be selected where necessary from various shapes including an elliptical shape, a quadrangular shape such as a square shape, an elongate rectangular shape, and a lozenge shape, a triangular shape, a hexagonal shape, and an octagonal shape.

A recess 434 is defined in the distal end of the holder 43, i.e., the portion thereof which confronts the test strip 53 in the tip mounted state (the portion facing the test strip 53 in the tip mounted state), with the first passage 431 (the opening 433) being positioned substantially centrally.

An annular recess 435 is defined around the recess 434 in communication with the recess 434 and deeper than the recess 434.

An O-ring 46 is placed in the annular recess 435, and a light-transmissive member 45 is placed and fixed in the recess 434. The first passage 431 and the second passage 432 (hereinafter simply referred to as "passage") in the holder 43 are sealed by the light-transmissive member 45 with the O-ring 46 interposed therebetween.

The light-transmissive member 45 may be fixed (secured) to the holder 43 by fitting, fusion bonding, threading, adhesive bonding, or the like.

In the tip mounted state, the light-transmissive member 45 isolates the test strip 53 and the passage in the holder 43 (the photometric unit 4) from each other.

If the passage in the holder 43 is not closed, i.e., if the passage is open at the distal end of the holder 43, then water or blood (specimen) spread in the test strip 53 may be unduly introduced into the passage. If water or blood is introduced, then it is difficult to remove the introduced water or blood, and the introduced water or blood tends to block the optical path or attenuate the amount of light, affecting the characteristics of the optical system. Therefore, the subsequent measurement of an amount of a blood component in question tends to be adversely affected, resulting in a reduction in the measurement accuracy.

According to the present invention, since the passage in the holder 43 is closed, water or blood (specimen) is reliably prevented from being introduced into the passage. Accordingly, it is possible to measure an amount of a blood component in question with a high level of measurement accuracy.

As the passage in the holder 43 remains securely closed, even when blood or the like is applied to the distal end face of the holder 43 (the photometric unit 4) or the light-transmissive member 45, it can easily and reliably be washed away by a cleaning liquid such as rubbing alcohol, and water.

As described above, the tip 5 is constructed with various features to prevent the blood supplied to the test strip 53 from being applied to the photometric unit 4. Since the component measuring device 1 according to the present invention allows blood deposits on the photometric unit 4 to be easily removed, the tip 5 may be of a simple structure and may be reduced in cost.

According to the present embodiment, the light-transmissive member 45 is in the form of a flat plate and has a distal end face (the face closer to the test strip 53) lying substantially flush with the distal end face of the holder 43. With this arrangement, when the light-transmissive member 45 is washed by the cleaning liquid, dust, blood, or the like is prevented from remaining near the boundary between the holder 43 and the light-transmissive member 45.

The thickness (average) of the light-transmissive member 45 slightly differs depending on the material thereof, and is not limited to any particular values. However, it should preferably be in the range from about 0.1 to 10 mm and more preferably in the range from about 0.3 to 3 mm. If the light-transmissive member 45 is too thin, its mechanical strength may be lowered. If the light-transmissive member 45 is too thick, then the photometric unit 4 is unfavorably large in size.

The light-transmissive member 45 should preferably be of a shape complementary to the opening 433, and should preferably be of a size large enough to cover the opening 433.

The light-transmissive member 45 may be made of any of various glass materials or various resin materials.

The holder 43 may be made of any of various resin materials including acrylic resin, polystyrene, polyethylene, polypropylene, hard polyvinyl chloride, polycarbonate, polymethyl methacrylate, ABS resin, polyester, polyphenylene sulfide (PPS), polyamide, polyimide, and polyacetal, or a polymer alloy, a polymer blend, or the like which contains one or more of the above resin materials, or any of various metal materials including aluminum, aluminum alloy, titanium, titanium alloy, and stainless steel.

The light-transmissive member 45 is not limited to a flat plate, but may be of a lens shape.

One or more coating layers for desired purposes may be provided on the surface of the light-transmissive member 45. The coating layer or layers may be provided for the purpose of increasing the measurement accuracy, or for the purpose of preventing the light-transmissive member 45 from being damaged, or the like.

For the purpose of increasing the measurement accuracy, the coating layer or layers may include an anti-reflection coating (AR coating) for preventing light emitted by the light-emitting element 42 from being reflected by the surface (proximal end surface) of the light-transmissive member 45, an anti-reflection coating for preventing reflected light reflected by the test strip 53 from being reflected by the surface (distal end surface) of the light-transmissive member 45, a low-pass filter for selectively passing light having a wavelength equal to or lower than 720 nm as disturbing light (particular, infrared radiation) greatly affects the measurement accuracy, a bandpass filter for selectively passing light having a wavelength in the range from about 500 to 720 nm (corresponding to the wavelength of light emitted from the light-emitting element 41), or the like.

For the purpose of preventing the light-transmissive member 45 from being damaged, the coating layer may include a reinforcing coating layer (hard coating layer) made primarily of an Si-based material, an Al-based material, a polyfunctional acrylic material, a urethane resin-based material, and a melamine resin-based material.

The O-ring 46 is made of an elastomeric material and has a diameter in the vertical cross section which is greater than the depth of the annular recess 435. When the light-transmissive member 45 is placed in the recess 434, the O-ring 46 is held in reliable contact with both the holder 43 and the light-transmissive member 45, thereby increasing the sealing (liquid-tight or air-tight sealing) of the passage in the holder 43 for further improving the advantages described above.

The elastomeric material may be any of various rubber materials (particularly those vulcanized) including natural rubber, isoprene rubber, butadiene rubber, styrene-butadiene rubber, nitrile rubber, chloroprene rubber, butyl rubber, acrylic rubber, ethylene-propylene rubber, hidrin rubber, urethane rubber, silicone rubber, and fluorocarbon rubber, or any of various plastic elastomers including styrene-based elastomer, polyolefin-based elastomer, polyvinyl chloride-based elastomer, polyurethane-based elastomer, polyester-based elastomer, polyamide-based elastomer, polybutadiene-based elastomer, transpolyisoprene-based elastomer, fluocarbon rubber-based elastomer, and chlorinated polyethylene-based elastomer. One or two or more of the above materials may be mixed together for use as the elastomeric material.

The O-ring 46 is not limited to the illustrated position, but may be positioned on an outer circumferential portion of the light-transmissive member 45.

Second Embodiment

A second embodiment of a component measuring device according to the present invention will be described below.

Figure 5:
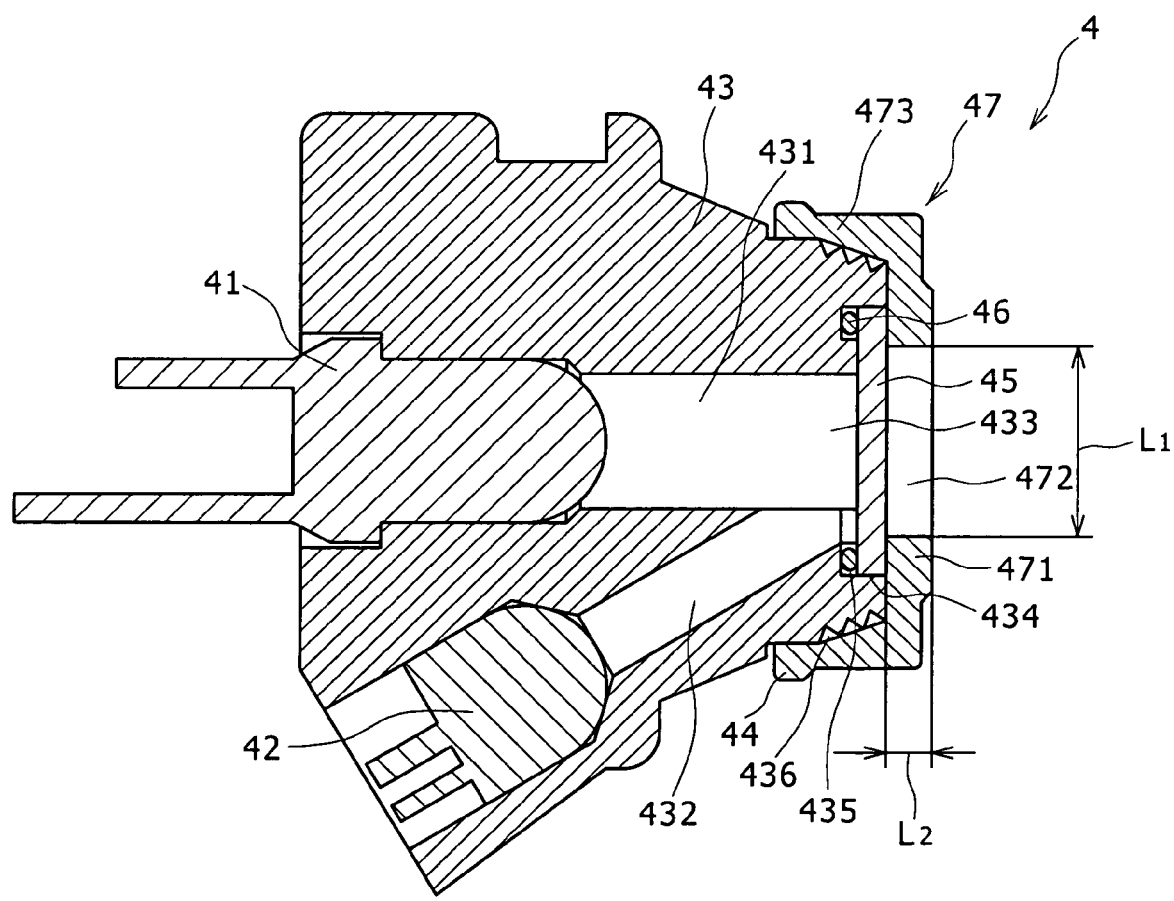
FIG. 5 is a vertical cross-sectional view showing the structure of a photometric unit of a second embodiment of a component measuring device according to the present invention.

FIG. 5 is a cross-sectional view showing the structure of the photometric unit of the second embodiment of the component measuring device according to the present invention.

The component measuring device according to the second embodiment will be described below basically with respect to differences thereof from the component measuring device according to the first embodiment, and identical parts will not be described below.

According to the second embodiment, the photometric unit 4 differs in structure. Other details of the second embodiment are identical to those of the first embodiment. Specifically, the photometric unit 4 shown in FIG. 5 differs from the photometric unit 4 according to the first embodiment in that a holder member 47 is added.

The holder member 47 serves to fix the light-transmissive member 45 to the holder 43. The holder member 47 includes an abutment portion 471 held in abutment against the light-transmissive member 45 and a barrel 473 integrally formed with the abutment portion 471.

The barrel 473 serves as a mount for mounting the holder member 47 on the distal end of the holder 43. Specifically, as shown in FIG. 5, the distal end of the holder 43 is inserted into the barrel 473 of the holder member 47 until the holder member 47 is mounted on (fitted over) the holder 43.

When the holder member 47 is mounted on the distal end of the holder 43 with the O-ring 46 placed in the annular recess 435 and the light-transmissive member 45 placed in the recess 434, the abutment portion 471 abuts against the light-transmissive member 45, and presses the light-transmissive member 45 toward the holder 43. The O-ring 46 presses the light-transmissive member 45 against the abutment portion 471 under its own resiliency. The light-transmissive member 45 is thus fixed to the holder 43.

An adhesive reservoir 436 in the form of a plurality of ring-shaped recesses is defined in the outer circumferential surface of the distal end of the holder 43. The adhesive reservoir 436 is supplied with an adhesive, fixing (securing) the holder member 47 to the holder 43.

The holder member 47 may be fixed (secured) to the holder 43 by fitting, fusion bonding, threading, or the like, rather than adhesive bonding. If the holder member 47 is fixed to the holder 43 by fitting or threading, then the light-transmissive member 45 and the O-ring 46 may conveniently be replaced when necessary.

The barrel 473 has a fitting portion 44 on the outer circumferential surface of the proximal end thereof for fitting engagement with the proximal end of the tip 5.

The abutment portion 471 is in the form of a flat plate having an opening 472 defined substantially centrally therein for passing therethrough light emitted from the light-emitting element 41 and reflected light reflected from the test strip 53.

The opening 472 has a cross-sectional shape that is of a substantially equal shape (similar shape) at any position from the distal end (outer end) to the proximal end (inner end), and has a substantially constant cross-sectional area from the distal end to the proximal end. Specifically, the angle formed between the inner surface of the opening 472 and the abutment portion 471 (the distal end and the proximal end of the abutment portion 471) is essentially 90°.

With this arrangement, even when a finger or the like is brought into contact with the distal end face of the holder member 47, the finger or the like is prevented from contacting the distal end face (outer face) of the light-transmissive member 45 (contact prevention capability).

The cross-sectional shape of the opening 472 should preferably be of substantially the same as the shape (as viewed in plan) of the light-transmissive member 45. The cross-sectional area (average) of the opening 472 should preferably be set to a value that is slightly smaller than the area of the light-transmissive member 45. With this arrangement, the light-transmissive member 45 is reliably pressed and fixed to the holder 43 by the abutment portion 471 (the holder member 47) without obstructing the passage of the light and the reflected light. The above contact prevention capability is also sufficiently performed.

From the above standpoint, the cross-sectional area (average) of the opening 472 should preferably be in the range from about 0.1 to 100 mm$^2$.

As shown in FIG. 5, if it is assumed that the maximum spaced distance between opposite inner surfaces of the opening 472 in the vertical cross section (the maximum diameter if the cross-sectional shape of the opening 472 is circular) is represented by $L_1$ [mm] and the thickness of the opening 72 (corresponding to the thickness of the abutment portion 471 according to the present embodiment) by $L_2$ [mm], then the ratio $L_2/L_1$ should preferably satisfy the relationship indicated by 0.1 or greater, and more preferably the relationship indicated by the range from 0.1 to 0.4. This allows the above contact prevention capability to be performed suitably.

The average thickness of the abutment portion 471 (the thickness of the opening 472) $L_2$ slightly differs depending on the material of the holder member 47, and is not limited to any particular values. However, it should preferably be in the range from about 0.1 to 10 mm. If the abutment portion 471 is too thin, then the mechanical strength of the abutment portion 471 (the holder member 47) tends to be lowered and the above contact prevention capability may not be sufficiently performed. If the thickness of the abutment portion 471 is increased in excess of the above upper limit, then the photometric unit 4 is unfavorably large in size.

The material of the holder member 47 may be the same as the material of the holder 43 as described above.

Third Embodiment

A third embodiment of a component measuring device according to the present invention will be described below.

Figure 6:
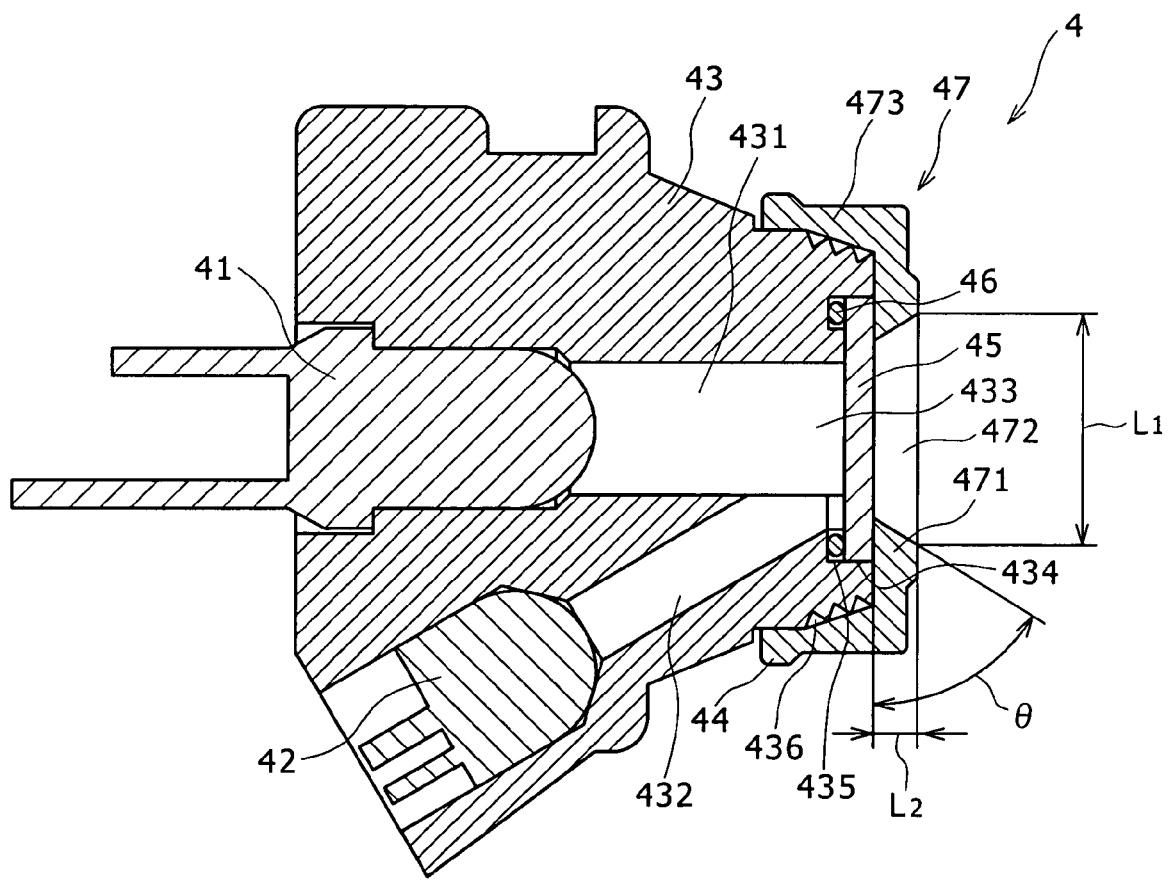
FIG. 6 is a vertical cross-sectional view showing the structure of a photometric unit of a third embodiment of a component measuring device according to the present invention.

FIG. 6 is a cross-sectional view showing the structure of the photometric unit of the third embodiment of the component measuring device according to the present invention.

The component measuring device according to the third embodiment will be described below basically with respect to differences thereof from the component measuring devices according to the first and second embodiments, and identical parts will not be described below.

According to the third embodiment, the holder member 47 differs in structure. Other details of the third embodiment are identical to those of the second embodiment. Specifically, the photometric unit 4 shown in FIG. 6 differs from the photometric unit 4 according to the second embodiment in that the opening 472 defined in the holder member 47 has a different shape.

The opening 472 according to the present embodiment has a cross-sectional shape that is of a substantially equal shape (similar shape) at any position from the distal end to the proximal end, and has a cross-sectional area that is progressively smaller continuously from the distal end to the proximal end. Specifically, the inner surface of the opening 472 is inclined at a certain angle ($\theta$ in FIG. 6) to the abutment portion 471 (the distal end face and the proximal end face of the abutment portion 471).

With this arrangement, even when dirt, blood, or the like is applied to the distal end face of the light-transmissive member 45 and the inner surface of the opening 472 or when a finger or the like is brought into contact with the distal end face of the light-transmissive member 45, applying fat (fingerprint) or the like thereto, the applied deposit can easily and reliably be removed.

According to the present embodiment, the opening area of the proximal end of the opening 472 should preferably be lightly smaller than the area of the light-transmissive member 45.

Particularly, as shown in FIG. 6, the opening area of the proximal end (inner end) of the opening 472 should preferably be greater than the opening area of the passage in the holder 43. With this arrangement, even if slight applied deposits remain in the vicinity of the boundary between the light-transmissive member 45 and the opening 472 when stains applied to the distal end face of the light-transmissive member 45 and the inner surface of the opening 472 are removed, the remaining stains are prevented from obstructing the light path of light from the light-emitting element 41 and reflected light reflected by the test strip 53, with the result that the measurement accuracy is prevented from being lowered.

The opening 472 may be of a structure whose cross-sectional area is reduced stepwise from the distal end to the proximal end, or may be of a structure having a portion whose cross-sectional area is reduced.

Fourth Embodiment

A fourth embodiment of a component measuring device according to the present invention will be described below.

Figure 10:
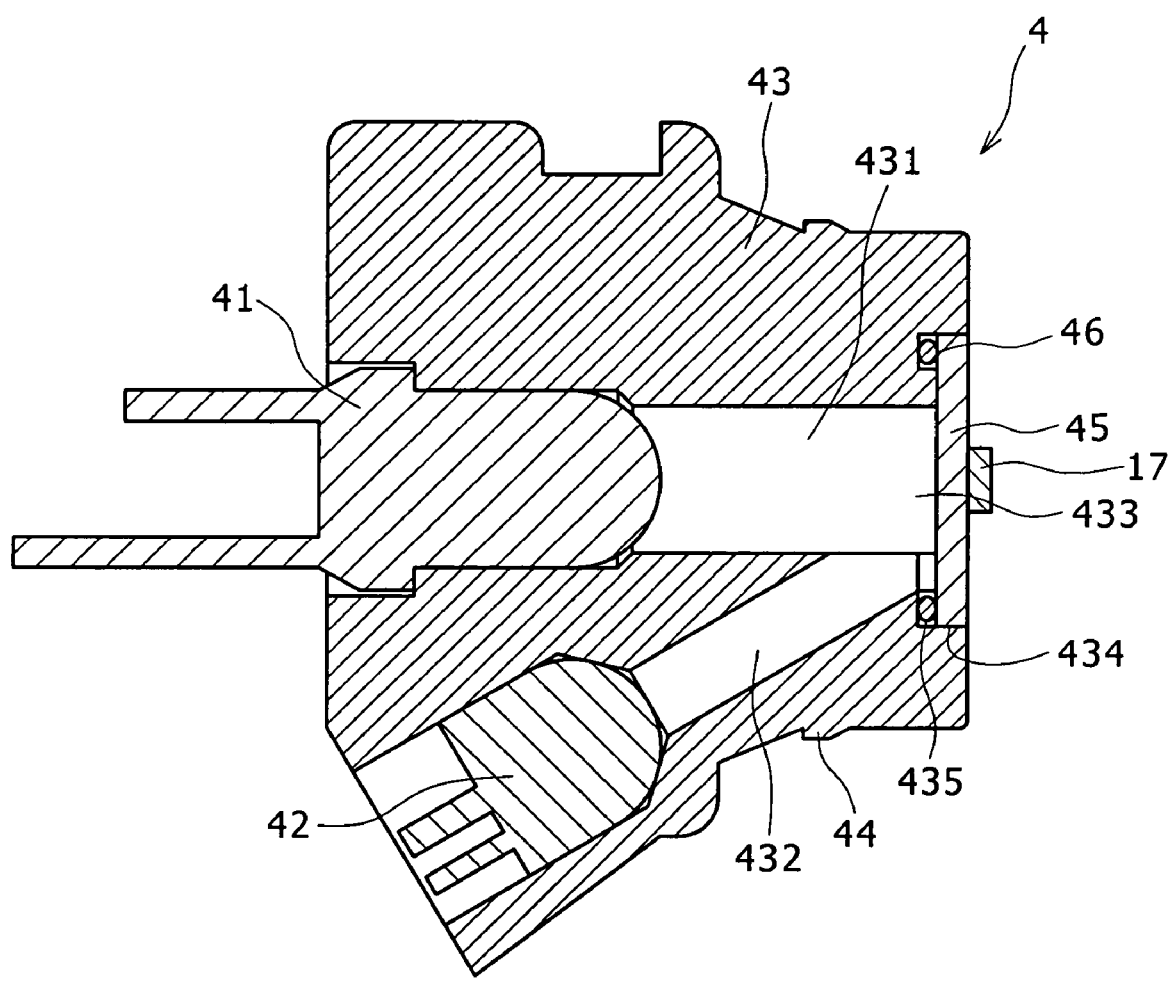
FIG. 10 is a vertical cross-sectional view showing the structure of a photometric unit of a fourth embodiment of a component measuring device according to the present invention.

FIG. 10 is a vertical cross-sectional view showing the structure of the photometric unit of the fourth embodiment of the component measuring device according to the present invention. FIG. 10 illustrates that a stain 17 is applied to the light-transmissive member 45. The left side in FIG. 10 will be referred to as "proximal end" and the right side as "distal end".

The component measuring device according to the fourth embodiment will be described below basically with respect to differences thereof from the component measuring devices according to the first embodiment, and identical parts will not be described below.

The component measuring device 1 according to the fourth embodiment has a stain detecting means for detecting a stain on the light-transmissive member 45. According to the fourth embodiment, the so-called black level checking process is employed to detect a stain on the light-transmissive member 45.

The liquid crystal display unit 9 also functions as indicating means for indicating the result of a process for detecting a stain on the light-transmissive member 45 as described later.

The second memory of the data storage unit 13 stores thresholds in addition to the relationship (analytical curve) between absorbances determined from photometric values and amounts of a blood component in question.

A process for detecting a stain on the light-transmissive member 45, which is an essential part (feature) of the component measuring device 1 according to the present embodiment, will be described below.

The component measuring device 1 is arranged to emit light from the light-emitting element 41 of the photometric unit 4, detect light with the light-detecting element 42, and detect a stain on the light-transmissive element 45 based on the amount of light detected by the light-detecting element 42.

In the process for detecting a stain on the light-transmissive member 45, light detected by the light-detecting element 42 is primarily emitted from the light-emitting element 41 and reflected by the light-transmissive element 45 and a stain such as dust, dirt, fingerprint, and blood, for example, applied thereto. As described above, the light-detecting element 42 outputs an analog signal depending on the amount of light detected thereby, and the analog signal is amplified and converted by the A/D converter 49 into a digital signal, which is input to the control means 10. Based on the input digital signal representative of the value depending on the amount of light detected by the light-detecting element 42, the control means performs a predetermined process (determination or the like) to detect a stain on the light-transmissive member 45. Therefore, the control means 10 serves as a main part of the stain detecting means.

The component measuring device 1 employs the so-called black level checking process to detect a stain on the light-transmissive member 45. The principles of the black level checking process will be described below.

If no stain is applied to the light-transmissive member 45 in an open state in which nothing is mounted on the distal end of the photometric unit 4 shown in FIG. 4, then light emitted from the light-emitting element 41 of the photometric unit 4 is not essentially applied to the light-detecting element 42 (there is no reflecting object).

If a stain 17 is applied to the light-transmissive member 45 in the open state as shown in FIG. 5, a portion of light emitted from the light-emitting element 41 of the photometric unit 4 is reflected by the stain 17, and weak reflected light is applied to the light-detecting element 42.

In the open state, therefore, the amount of light detected by the light-detecting element 42 is greater as more stain is applied to the light-transmissive member 45.

If a black (dark) pattern is put on the distal end (distal end side) of the photometric unit 4, then since light emitted from the light-emitting element 41 is not essentially reflected by the black pattern, the amount of light detected by the light-detecting element 42 is greater as more stain is applied to the light-transmissive member 45.

In the process for detecting a stain on the light-transmissive member 45 according to the present embodiment, with the tip 5 being not mounted on the distal end of the photometric unit 4, e.g., in the open state with nothing mounted on the distal end of the photometric unit 4, or in a test tip mounted state in which a light-shielding test tip, described later, is mounted on the distal end of the photometric unit 4, light is emitted from the light-emitting element 41 of the photometric unit 4, light is detected by the light-detecting element 42, and a stain on the light-transmissive member 45 is detected based on the amount of light detected by the light-detecting element 42. If the amount of light detected by the light-detecting element 42 is greater than a preset threshold, then it is determined that there is a stain on the light-transmissive member 45. The threshold may be experimentally determined depending on various conditions, for example.

According to the present invention, the phrase "the amount of light detected by the light-detecting element 42 is greater than a preset threshold" includes not only a>b, but also a≧b where "a" represents the amount of light detected by the light-detecting element 42 and "b" the threshold. Therefore, it may be determined that there is a stain on the light-transmissive member 45 if a>b, or it may be determined that there is a stain on the light-transmissive member 45 if a≧b.

Advantages of the black level checking process over the white level checking process will be described below.

Figure 11:
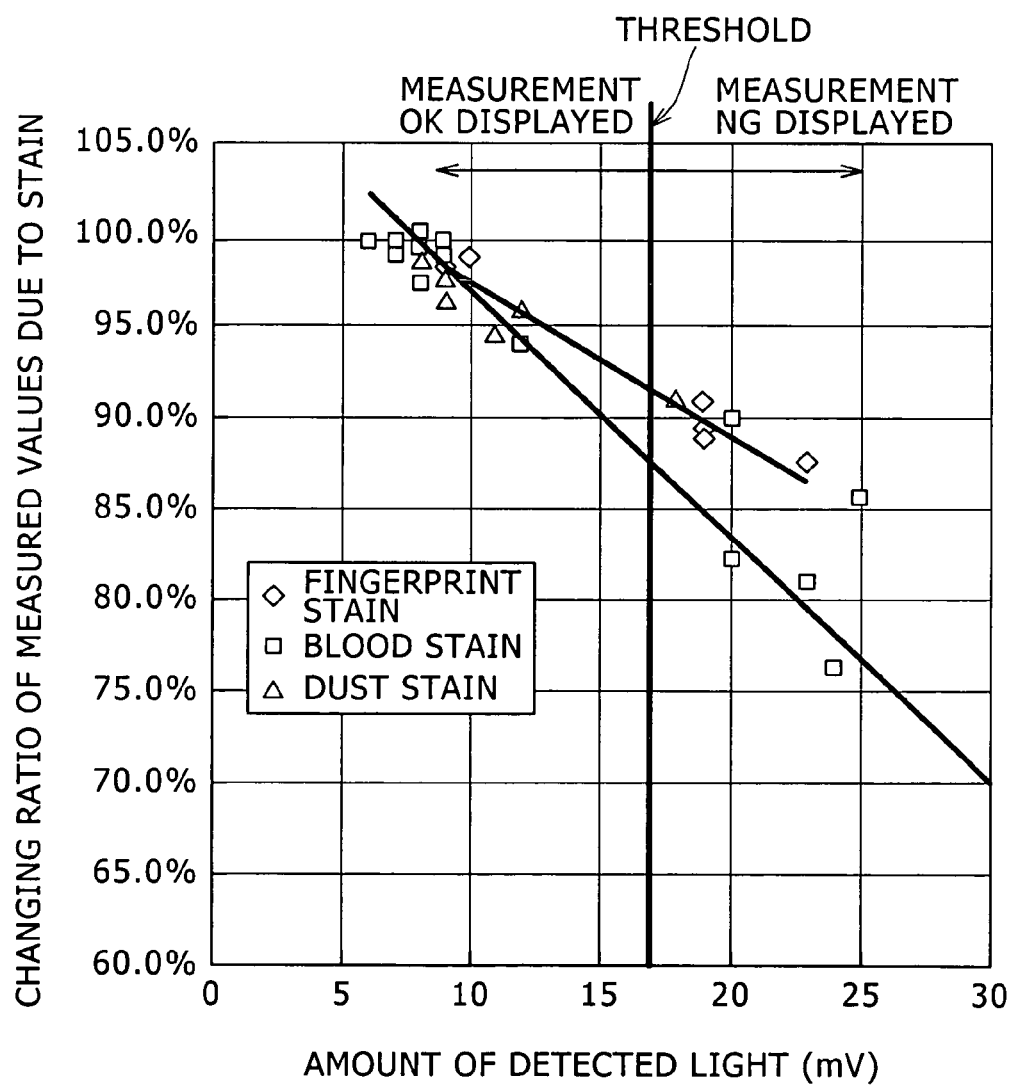
FIG. 11 is a graph showing characteristic curves plotted according to a black level checking process when stains (stained states) of a light-transmissive member are changed.
Figure 12:
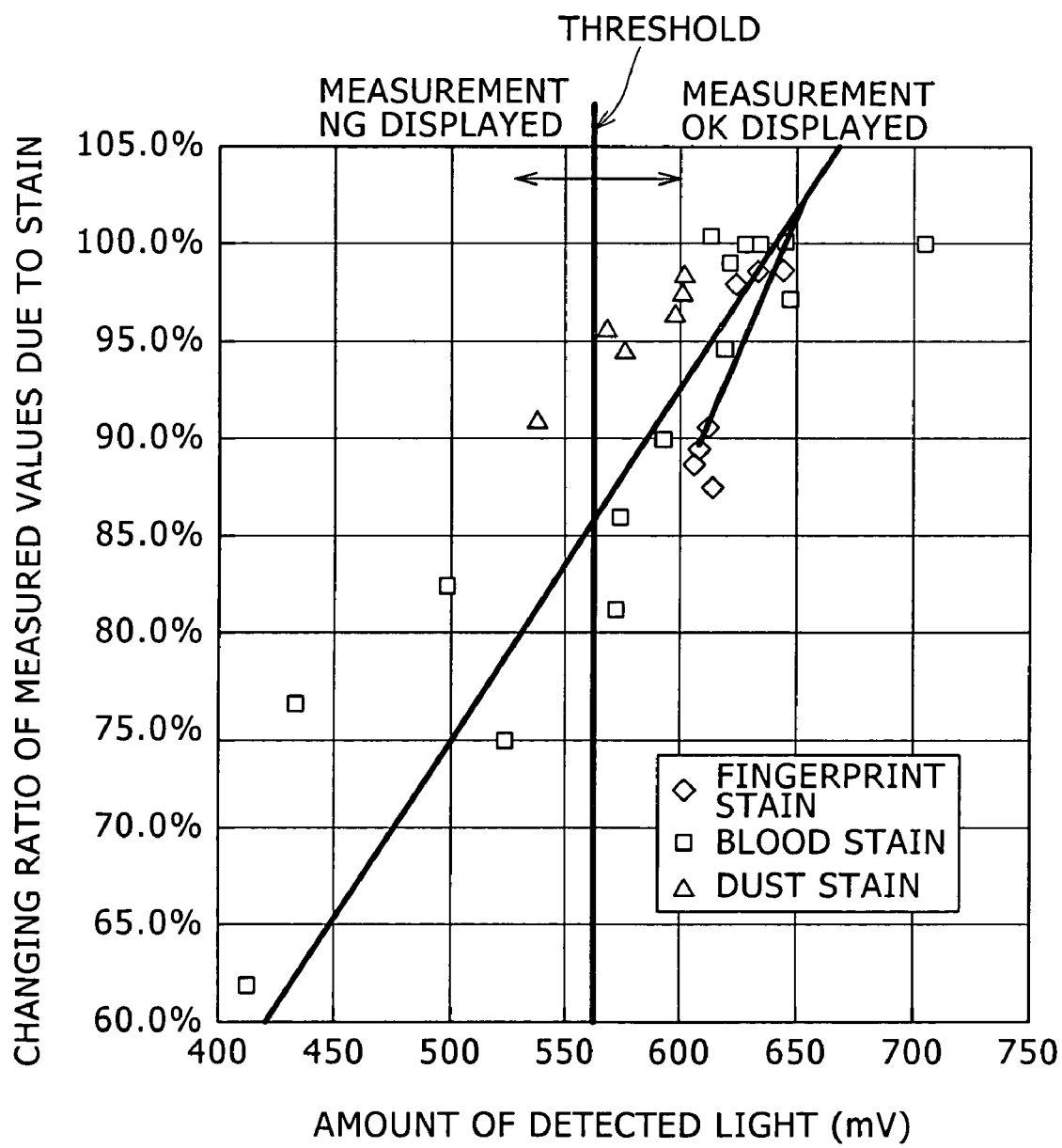
FIG. 12 is a graph showing characteristic curves plotted according to a white level checking process when stains (stained states) of a light-transmissive member are changed.

FIG. 11 is a graph showing characteristic curves plotted according to the black level checking process when stains (stained states) of the light-transmissive member 45 are changed. FIG. 12 is a graph showing characteristic curves plotted according to the white level checking process when stains (stained states) of the light-transmissive member are changed.

In the graph of FIG. 11, the vertical axis represents the changing ratio of measured values due to stains, and the horizontal axis the amount of light detected by the light-detecting element 42 when a light-shielding test tip, described later, is mounted on the distal end of the photometric unit 4.

In the graph of FIG. 12, the vertical axis represents the same changing ratio as with FIG. 11, and the horizontal axis the amount of light detected by the light-detecting element when an unused tip 5 is mounted on the distal end of the photometric unit.

According to the white level checking process, as shown in FIG. 12, if a threshold value is set as shown, for example, the changing ratio may possibly be in the range from 80% to 90% even when a measurement OK is displayed. It is difficult to set a threshold for appropriately detecting a stain.

However, according to the black level checking process, as shown in FIG. 11, the changing ratio of measured values and the amount of light detected by the light-detecting element 42 are highly correlated, making it easy to set a threshold for accurately detecting a stain.

A test tip for use in detecting a stain on the light-transmissive member 45 will be described below.

Figure 13:
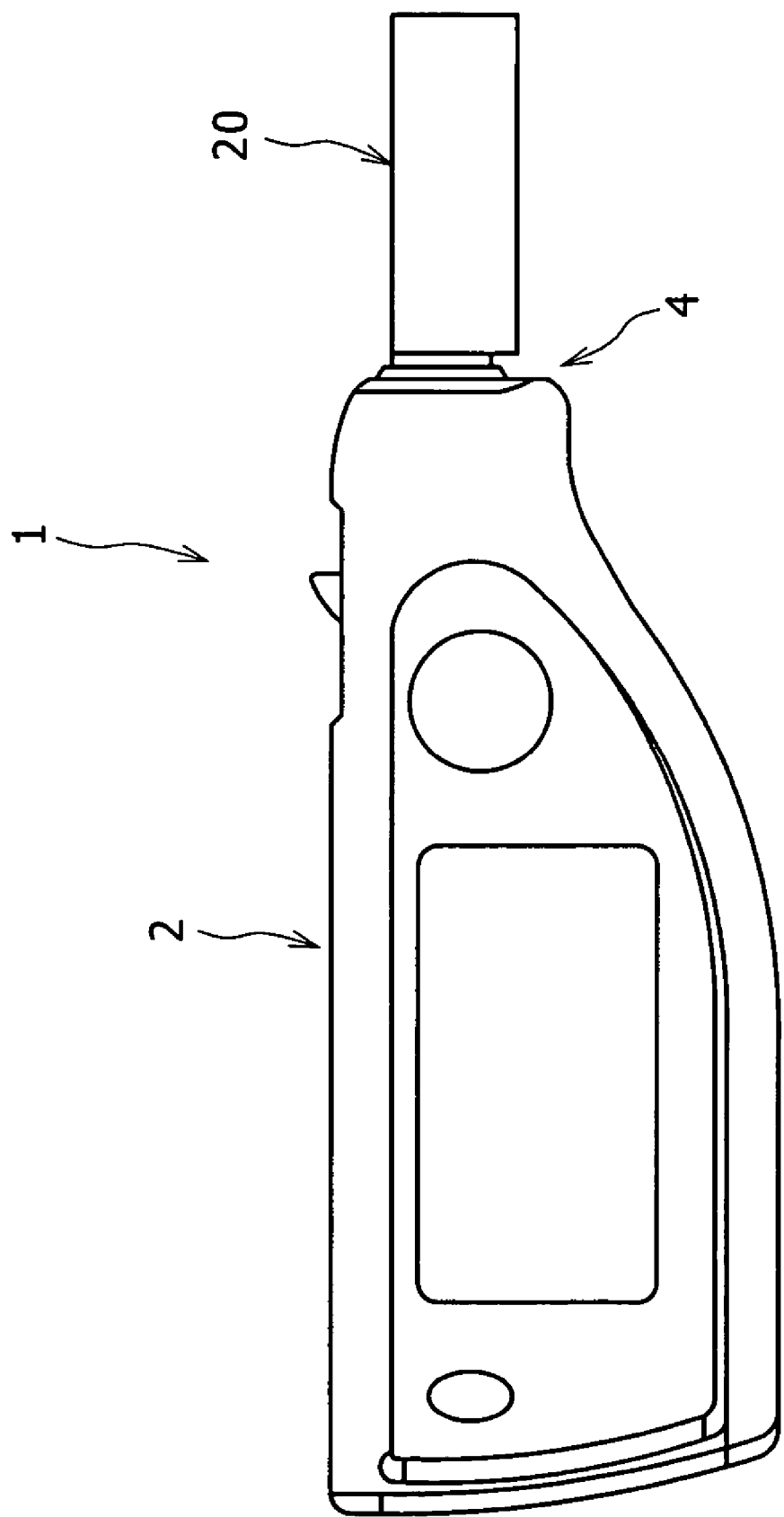
FIG. 13 is a plan view of an embodiment (arrangement) of a test tip mounted on the component measuring device according to the fourth embodiment.
Figure 14:
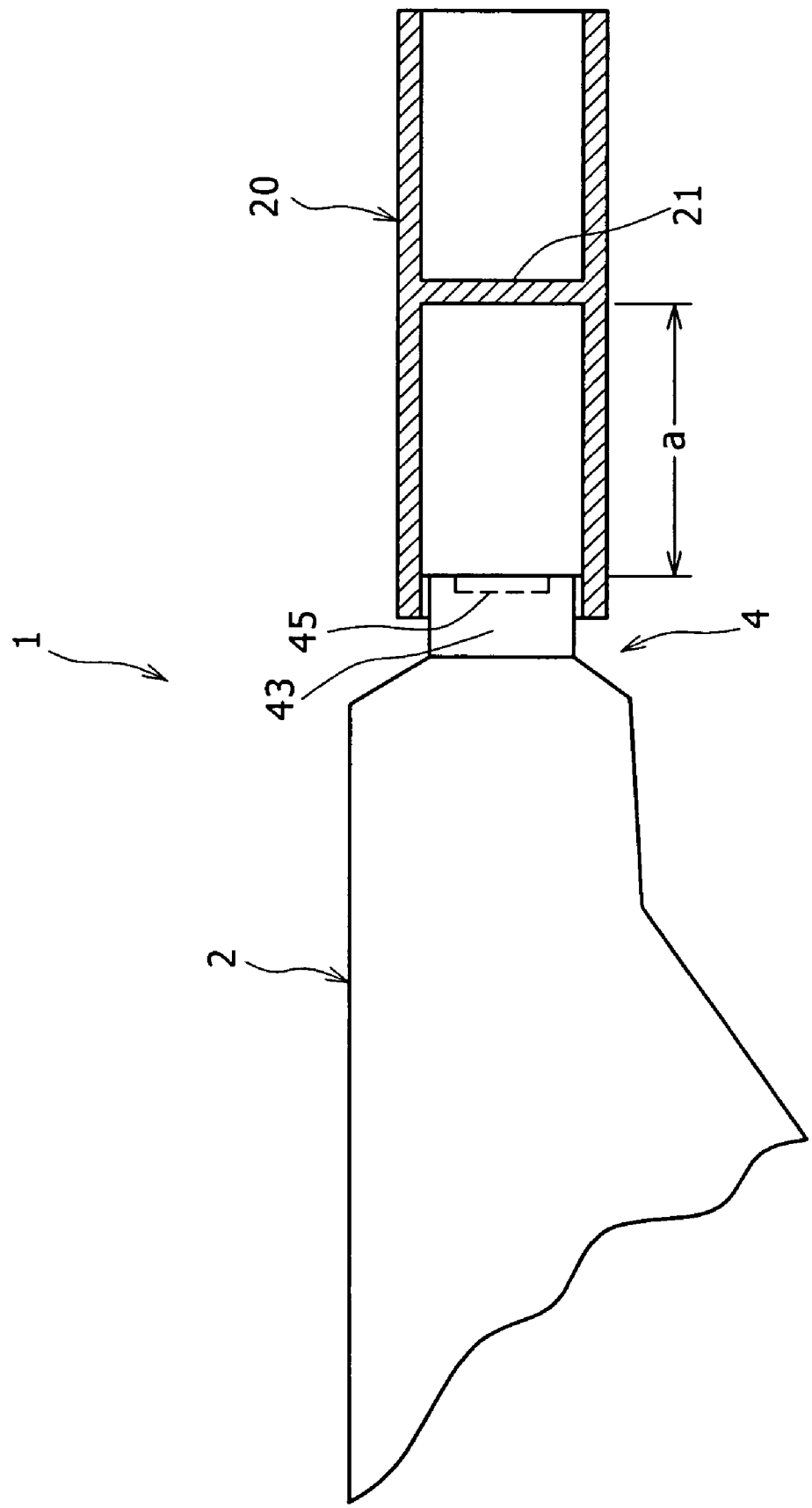
FIG. 14 is a sectional plan view of the test tip shown in FIG. 13.

FIG. 13 is a plan view of an embodiment (arrangement) of a test tip mounted on the component measuring device according to the fourth embodiment, and FIG. 14 is a sectional plan view of the test tip shown in FIG. 13. The left side in FIGS. 13 and 14 will be referred to as "proximal end" and the right side as "distal end".

As shown in FIGS. 13 and 14, a test tip (lid) 20 is light-shielding and is removably mounted on the distal end of the photometric unit 4.

According to the present invention, the test tip 20 is of a hollow cylindrical shape (tubular shape) and has a partition 21 disposed therein. For mounting the test tip 20 on the distal end of the photometric unit 4, the proximal end of the test tip 20 is fitted over the distal end of the photometric unit 4. The partition 21 of the test tip 20 and the proximal end of the partition 21 provide a lid-like member for covering the tip portion of the distal end of the photometric unit 4.

The test tip 20 may be black or dark in color, but should preferably be black. Though the test tip 20 may be black or dark in its entirety, only the lid-like member of the test tip 20 may be black or dark.

With the test tip 20 mounted on the distal end of the photometric unit 4, light emitted from the light-emitting element 41 is prevented from being reflected by the test tip 20 and external light is prevented from entering the test tip 20. Thus, unwanted light is prevented from being applied to the light-detecting element 42.

When the test tip 20 is mounted on the distal end of the photometric unit 4, the length "a" from the tip of the distal end of the photometric unit 4 to the inner wall of the partition 21 of the test tip 20 should preferably be 10 mm or greater.

With the length "a" being 10 mm or greater, it is possible to reliably prevent light emitted from the light-emitting element 41 from being reflected by the test tip 20 and applied to the light-detecting element 42 (an ideal non-reflected state or a state highly close thereto is achieved).

The test tip 20 is not limited to the illustrated shape, but may be of a shape suited to the component measuring device 1 for mounting the test tip 20 thereon.

The test tip 20 is not limited to any materials, but may be made of a rigid material having a predetermined level of rigidity, for example. The rigid material may be any of various resin materials including acrylic resin, polystyrene, polyethylene, polypropylene, hard polyvinyl chloride, polycarbonate, polymethyl methacrylate, ABS resin, polyester, polyphenylene sulfide (PPS), polyamide, polyimide, polyacetal, etc., or a polymer alloy, a polymer blend, or the like which contains one or more of the above resin materials.

The component measuring device 1 has a normal measurement mode for making measurements and a stain detecting mode for detecting a stain on the light-transmissive member 45.

When the power supply switch is turned on (the power supply is turned on) while the time setting/changing switch is being turned on, the component measuring device 1 is set to the stain detecting mode. When the power supply switch is turned on while the time setting/changing switch is being turned off, the component measuring device 1 is set to the normal measurement mode.

Figure 15:
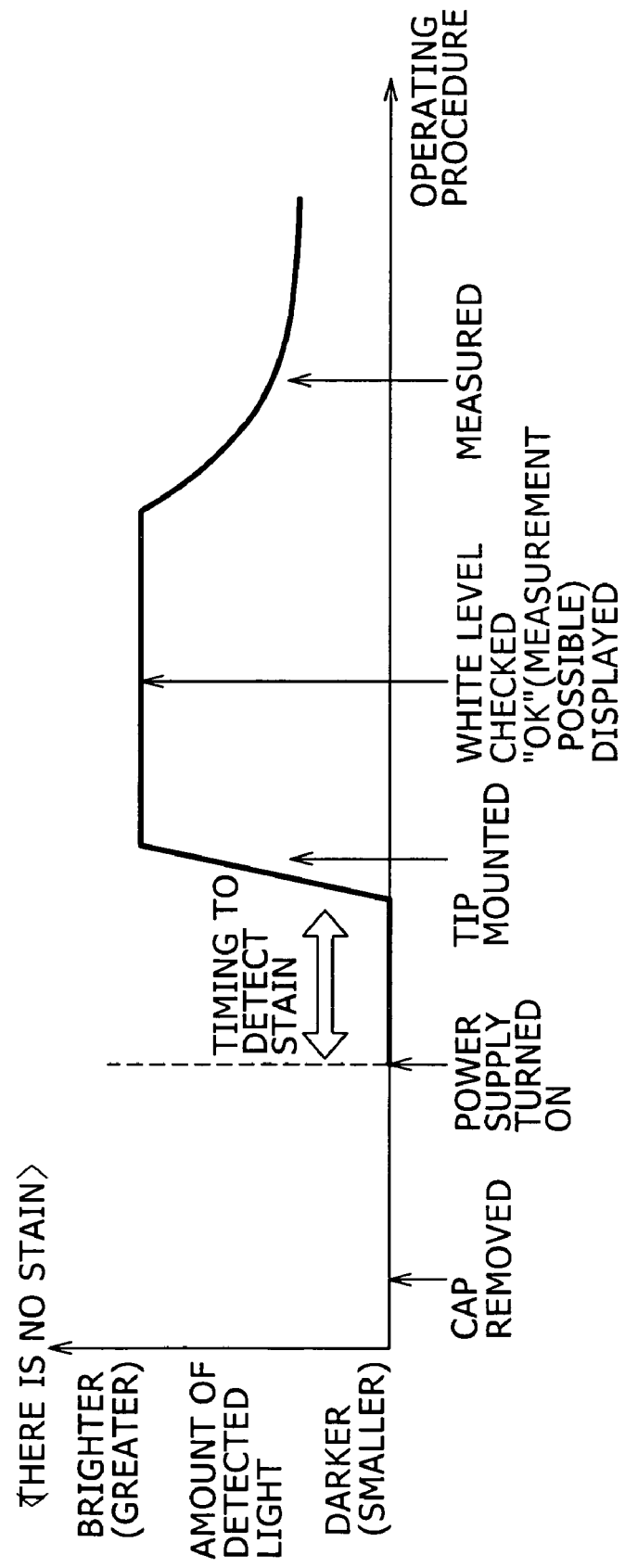
FIG. 15 is a timing chart showing the relationship between the amount of light detected by a light-detecting element when there is no stain on a light-transmissive member and an operating procedure in a normal measurement mode.
Figure 16:
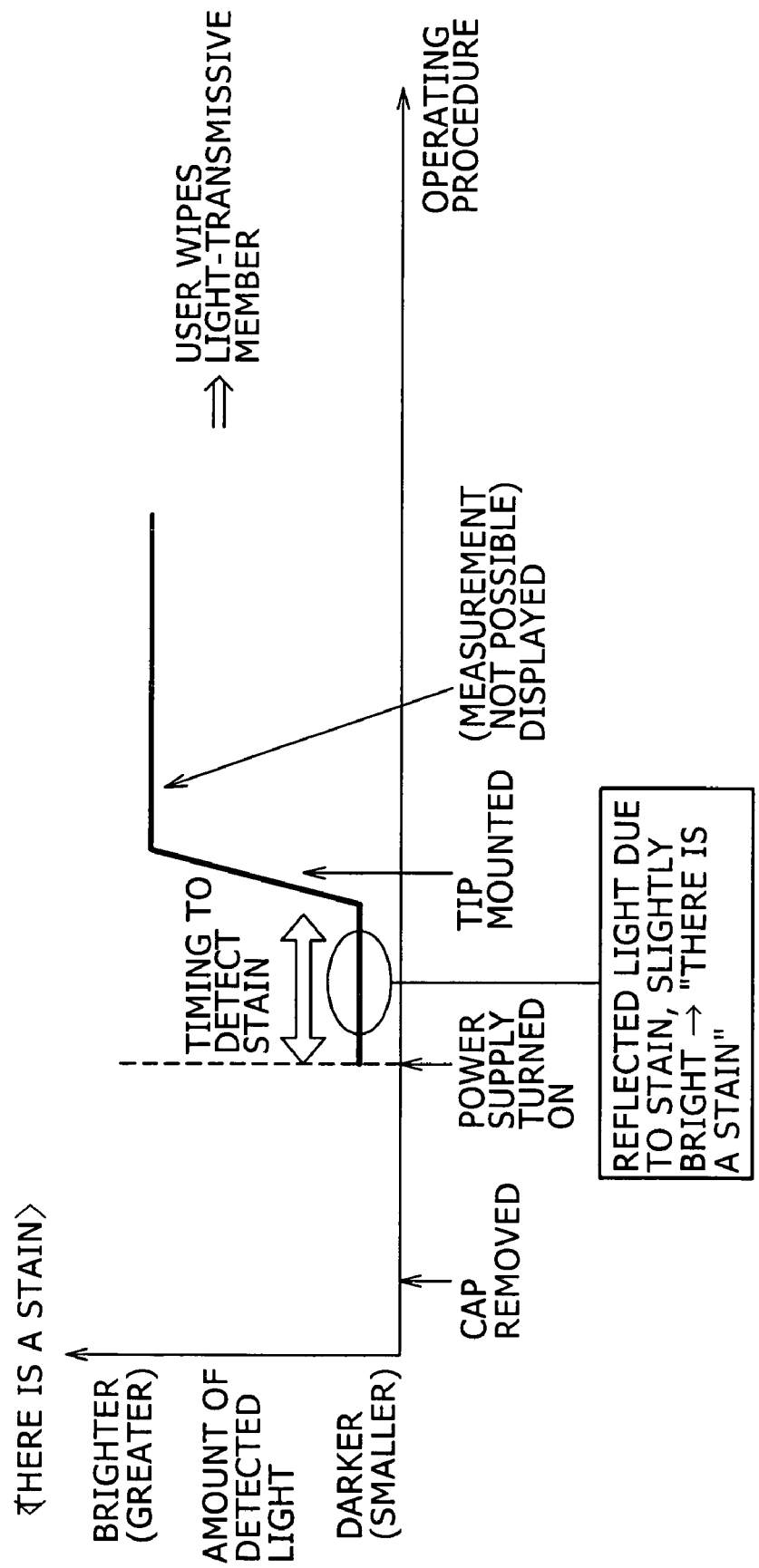
FIG. 16 is a timing chart showing the relationship between the amount of light detected by a light-detecting element when there is a stain on a light-transmissive member and an operating procedure in a normal measurement mode.
Figure 17:
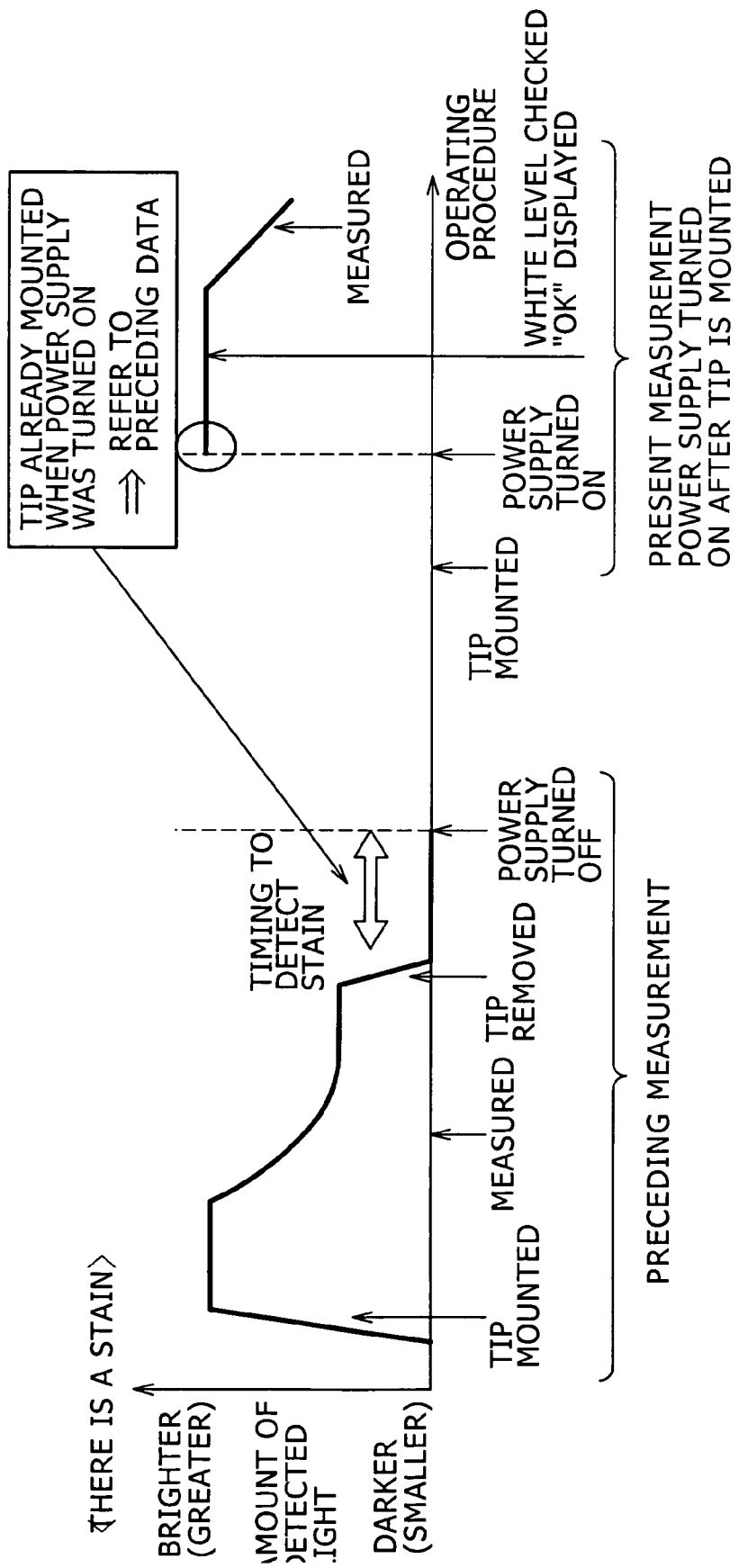
FIG. 17 is a timing chart showing the relationship between the amount of light detected by a light-detecting element 42 and an operating procedure in a normal measurement mode.

FIG. 15 is a timing chart showing the relationship between the amount of light detected by the light-detecting element 42 when there is no stain on the light-transmissive member 45 and an operating procedure in the normal measurement mode. FIG. 16 is a timing chart showing the relationship between the amount of light detected by the light-detecting element 42 when there is a stain on the light-transmissive member 45 and the operating procedure in the normal measurement mode. FIG. 17 is a timing chart showing the relationship between the amount of light detected by the light-detecting element 42 and the operating procedure in the normal measurement mode. FIGS. 15, 16, and 17 show the amount of light detected by the light-detecting element 42 on the assumption that light is emitted from the light-emitting element 41 even when light is not actually emitted from the light-emitting element 41.

In the normal measurement mode, when the power supply switch is turned on, as shown in FIG. 15, the above stain detecting process is performed if the tip 5 is not mounted on the distal end of the photometric unit 4.

It is determined whether there is a stain or not based on the amount of light detected by the light-detecting element 42.

If it is determined that there is no stain, then when the tip 5 is mounted on the distal end of the photometric unit 4, the liquid crystal display unit 9 displays "OK" indicating that measurements are possible.

It is determined whether the tip 5 is mounted or not based on the amount of light detected by the light-detecting element 42. Specifically, if the tip 5 is mounted, then the amount of light detected by the light-detecting element 42 is greater than if the tip 5 is not mounted. Therefore, a predetermined value is established, and if the amount of light detected by the light-detecting element 42 is greater than the predetermined value, then it is determined that the tip 5 is mounted, and if the amount of light detected by the light-detecting element 42 is smaller than the predetermined value, then it is determined that the tip 5 is not mounted.

When the operator (user) sees the displayed "OK", the operator can recognize that there is no stain and measurements are possible, and performs the predetermined operating procedure described above.

When the blood is spread into the test strip 53 in the tip 5, the amount of light detected by the light-detecting element 42 is reduced.

If there is a stain, as shown in FIG. 16, then when the tip 5 is mounted on the distal end of the photometric unit 4, the liquid crystal display unit 9 displays (turns on) a warning indicating that there is a stain and no measurements are possible.

When the operator sees the warning, the operator can recognize that there is a stain and no measurements are possible, and wipes or cleans the light-transmissive member 45, thereby removing the stain from the light-transmissive member 45.

In the normal measurement mode, as shown in FIG. 17, when the measurement is over and the tip 5 is removed from the distal end of the photometric unit 4, the above stain detecting process is performed. The result of the stain detecting process is stored in the third memory of the data storage unit 13.

When the power supply switch is turned off (the power supply is shut down) and then turned on again, if the tip 5 is mounted on the distal end of the photometric unit 4, i.e., when power supply switch is turned on with the tip 5 mounted in place, no stain detecting process is performed, and the information stored in the third memory (the result of the stain detecting process after the preceding measurement is finished) is used.

Specifically, if the result of the stain detecting process after the preceding measurement is finished indicates no stain, then the liquid crystal display unit 9 displays "OK" indicating that measurements are possible.

If the result of the stain detecting process after the preceding measurement is finished indicates a stain, then the liquid crystal display unit 9 displays (turns on) a warning indicating that there is a stain and no measurements are possible.

In the stain detecting mode, when the power supply switch is turned on, the liquid crystal display unit 9 displays that the stain detecting mode is set.

The user mounts the test tip 20 on the distal end of the photometric unit 4. Then, when a call switch is turned on, the stain detecting process is performed.

If there is no stain, then the liquid crystal display unit 9 displays "YES" indicating that there is no stain.

When the user sees the displayed "YES", the user can recognize that there is no stain.

If there is a stain, then the liquid crystal display unit 9 displays "NO" indicating that there is a stain.

When the user sees the displayed "NO", the user can recognize that there is a stain, and wipes or cleans the light-transmissive member 45, thereby removing the stain from the light-transmissive member 45. The user then operates to perform the stain detecting process, thereby performing the stain detecting process.

The stain detecting mode includes a detailed stain detecting mode for displaying a stain level (e.g., a numerical value thereof). When the calling switch is turned on while the time setting/changing switch is being turned on in the stain detecting mode, the detailed stain detecting mode is set.

In the detailed stain detecting mode, as in the stain detecting mode, the user mounts the test tip 20 on the distal end of the photometric unit 4. Then, when the call switch is turned on, the stain detecting process is performed.

If there is no stain, then the liquid crystal display unit 9 displays "YES" indicating that there is no stain.

If there is a stain, then the liquid crystal display unit 9 displays "NO" indicating that there is a stain and also displays the amount of light detected by the light-detecting element 42 as a numeral indicative of the level of the stain.

When the user sees the value (numeral) of the amount of light detected by the light-detecting element 42 as displayed by the liquid crystal display unit 9, the user can recognize the stain level and can take an appropriate action depending on the stain level.

A control process (operation) of the control means 10 of the component measuring device 1 will be described below with reference to FIGS. 18 through 20.

Figure 18:
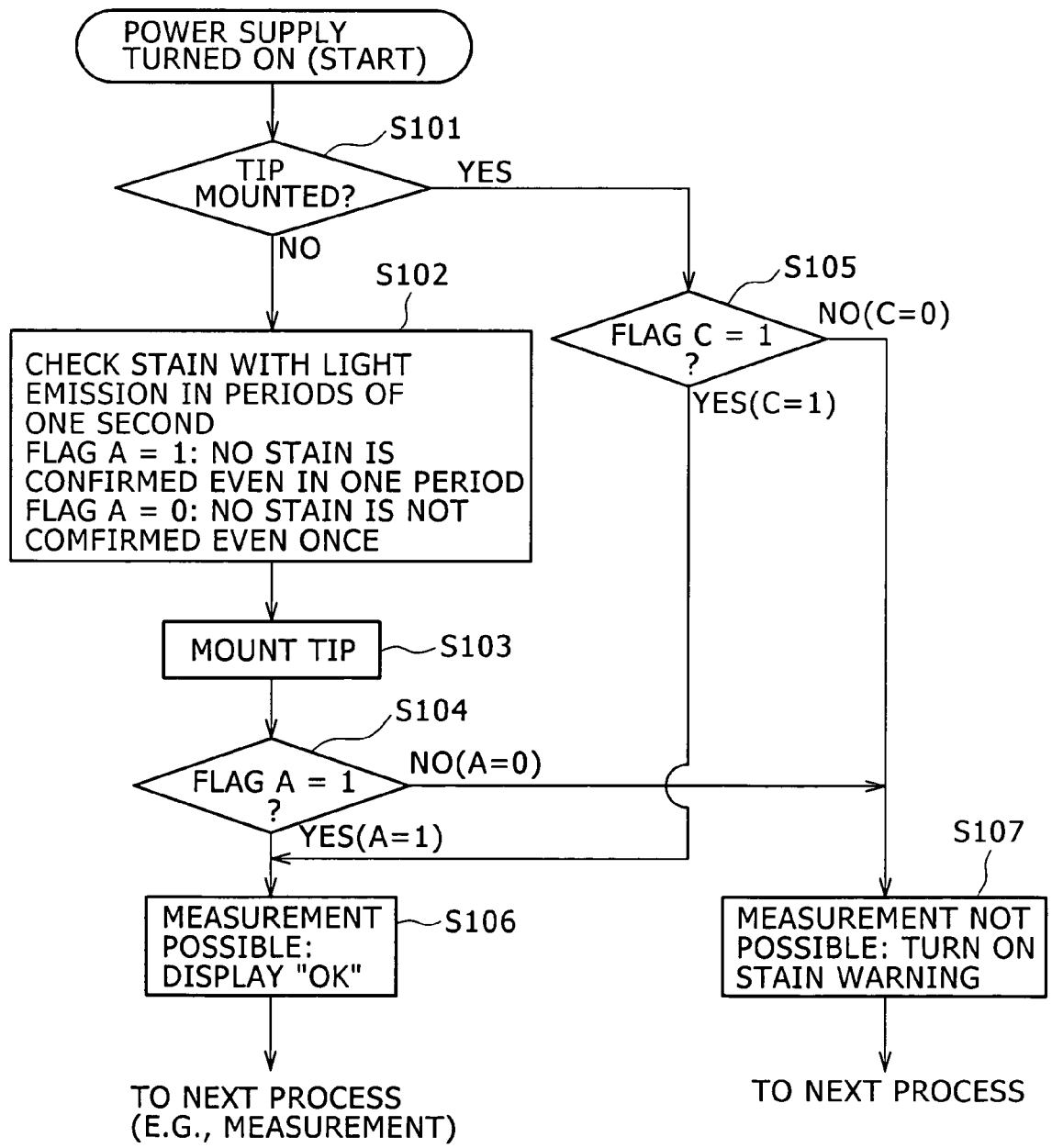
FIG. 18 is a flowchart of a control process of a control means of the component measuring device according to the fourth embodiment.
Figure 19:
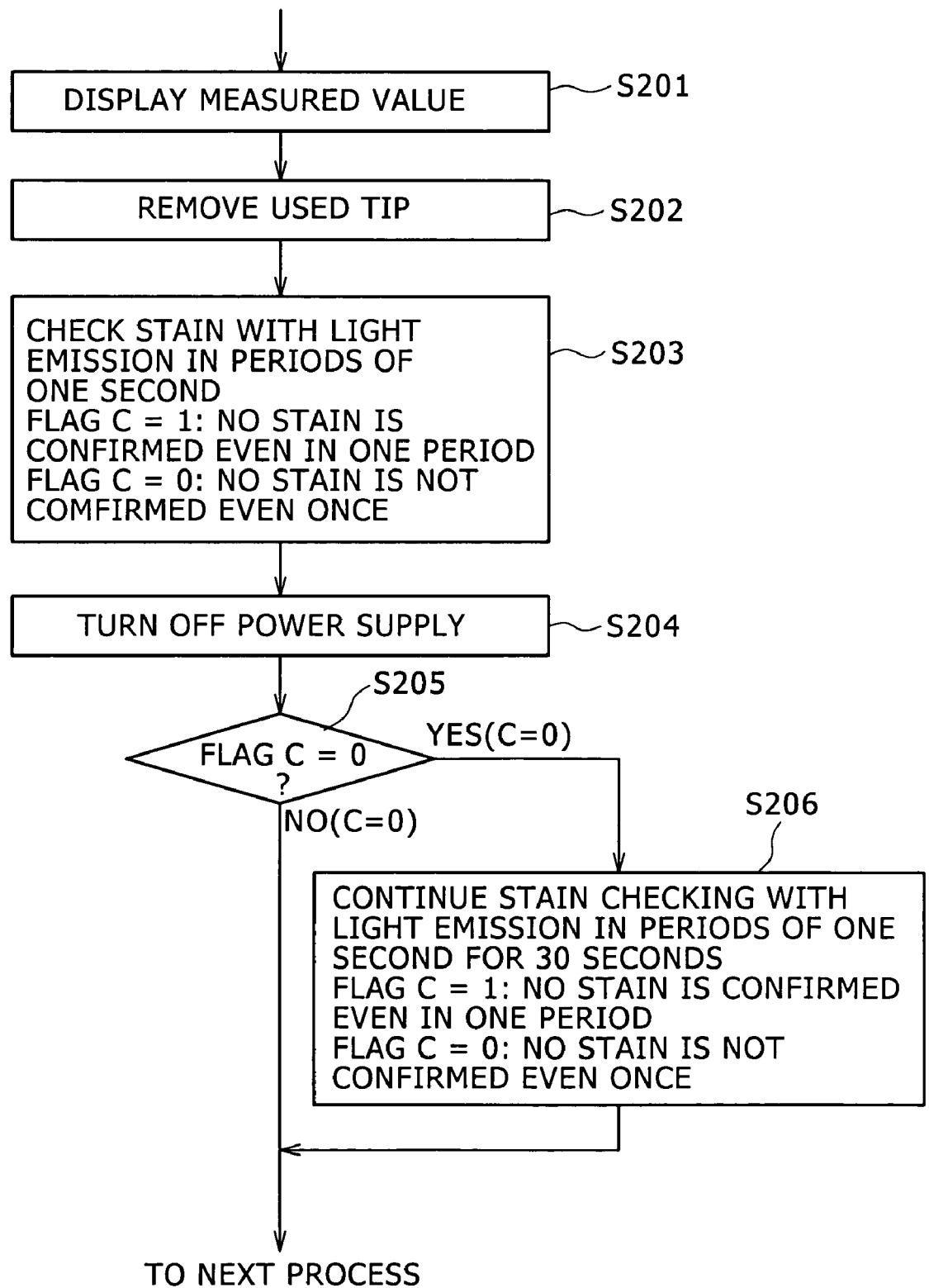
FIG. 19 is a flowchart of the control process of the control means of the component measuring device according to the fourth embodiment.
Figure 20:
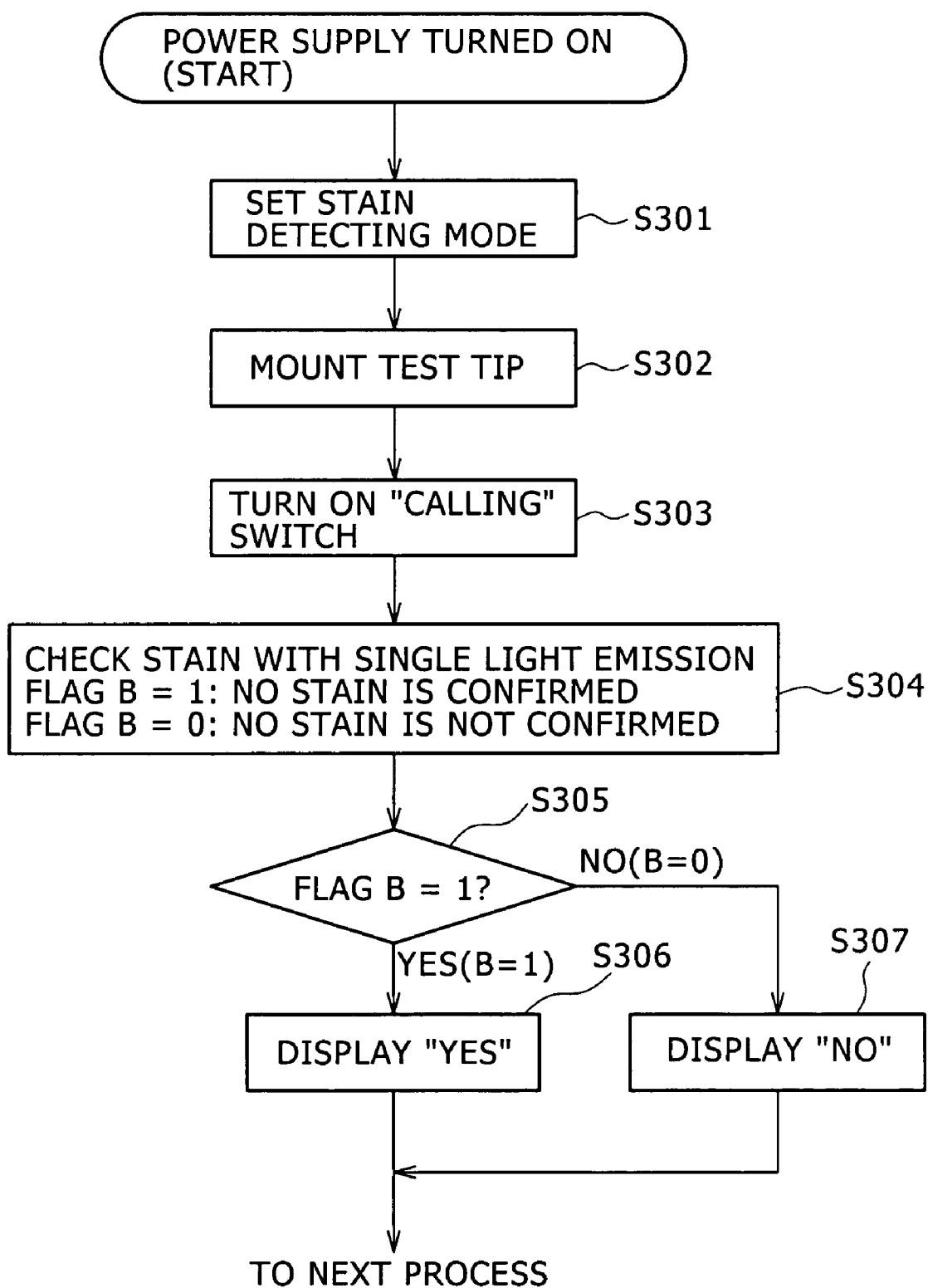
FIG. 20 is a flowchart of the control process of the control means of the component measuring device according to the fourth embodiment.

FIGS. 18 through 20 are flowcharts a control process of the control means 10 of the component measuring device 1 according to the fourth embodiment. FIGS. 18 and 19 show the control process in the normal measurement mode, and FIG. 20 shows the control process in the stain detecting mode. For a simpler description and an easier understanding of the invention, some determining (judging) steps are shown as normal steps and some user's actions are shown as steps in FIGS. 18 through 20.

First, the control process of the control means 10 of the component measuring device 1 in the normal measurement mode will be described below.

As described above, when the power supply switch is turned on while the time setting/changing switch is being turned off, the component measuring device 1 is set to the normal measurement mode. As shown in FIG. 18, it is determined whether the tip 5 is mounted on the distal end of the photometric unit 4 or not (step S101). If the tip 5 is mounted, then control goes to step S105, and if the tip 5 is not mounted, then control goes to step S102.

In step S102, the light-emitting element 41 is intermittently energized a plurality of times in periods of one second, and the above stain detecting process is performed in each of the periods.

If no stain is confirmed even in one of the periods in which the stain detecting process is performed, then it is determined that there is no stain, and a flag A indicative of no stain is set (A=1).

If no stain is not confirmed even in one of the periods in which the stain detecting process is performed (the amount of light detected by the light-detecting element 42 is greater than the preset threshold in all of the periods in which the stain detecting process is performed), it is determined that there is a stain, and the flag A is not set (A=0).

The emission of light from the light-emitting element 41 in step S102 is not limited to periods of one second.

Then, when the tip 5 is mounted on the distal end of the photometric unit 4 (step S103), it is determined whether the flag A=1 or not (step S104). If the flag A=1, then the liquid crystal display unit 9 displays "OK" indicating that there is no stain and measurements are possible (step S106), after which control goes to a next process (e.g., measurement).

If A=0, then the liquid crystal display unit 9 displays (turns on) a stain warning indicating that there is a stain and no measurements are possible (step S107), after which control goes to a next process.

In step S105, it is determined whether a flag C=1 or not. If the flag C=1, then control goes to step S106 to carry out step S106 and the following process. If the flag C=0, then control goes to step S107 to carry out step S107 and the following process.

The flag C will be described later. The information of the flag C (whether the flag C is 1 or 0) is stored in the third memory of the data storage unit 13, and will not be erased even when the power supply switch is turned off. The information of the flag C is read from the third memory prior to the decision in step S105.

As shown in FIG. 19, the measurement is over and the measured value is displayed by the liquid crystal display unit 9 (step S201), and the used tip 5 is removed from the distal end of the photometric unit 4 (step S202). The light-emitting element 41 is intermittently energized a plurality of times in periods of one second, and the above stain detecting process is performed in each of the periods (step S203).

If no stain is confirmed even in one of the periods in which the stain detecting process is performed, then it is determined that there is no stain, and the flag C indicative of no stain is set (C=1). The information of the flag C(C=1) is stored in the third memory of the data storage unit 13.

If no stain is not confirmed even in one of the periods in which the stain detecting process is performed (the amount of light detected by the light-detecting element 42 is greater than the preset threshold in all of the periods in which the stain detecting process is performed), it is determined that there is a stain, and the flag C is not set (C=0). The information of the flag C(C=0) is stored in the third memory of the data storage unit 13.

The emission of light from the light-emitting element 41 in step S203 is not limited to periods of one second.

Then, when the power supply switch is turned off (step S204), it is determined whether the flag C=1 or not (step S205). If the flag C=1, then control goes to a next process. Strictly, the power supply switch is turned off after the necessary process is finished.

If the flag C=0, control goes to step S206 to be described below. After having performed step S206, control goes to a next process.

If the used tip 5 is not removed from the distal end of the photometric unit 4 in step 202, step S203 is not performed, and the flag C=0.

Specifically, when the power supply switch is turned off with the used tip 5 being mounted on the distal end of the photometric unit 4 (step S204), it is determined that the flag C=0 in step S205, and control goes to step S206.

In step S206, the light-emitting element 41 is intermittently energized a plurality of times in periods of one second (for 30 seconds), and the above stain detecting process is performed in each of the periods.

If no stain is confirmed even in one of the periods in which the stain detecting process is performed, then it is determined that there is no stain, and the flag C indicative of no stain is set (C=1). The information of the flag C(C=1) is stored in the third memory of the data storage unit 13.

If no stain is not confirmed even in one of the periods in which the stain detecting process is performed (the amount of light detected by the light-detecting element 42 is greater than the preset threshold in all of the periods in which the stain detecting process is performed), it is determined that there is a stain, and the flag C is not set (C=0). The information of the flag C(C=0) is stored in the third memory of the data storage unit 13.

As described above, even when the power supply switch is turned off with the used tip 5 being mounted on the distal end of the photometric unit 4, the stain detecting process is performed in step S206.

The emission of light from the light-emitting element 41 in step S206 is not limited to periods of one second, and the time in which the emission of light from the light-emitting element 41 is continued is not limited to 30 seconds.

The information of the flag C stored in the third memory of the data storage unit 13 (whether the flag C is 1 or 0) will be used in the decision of step S105 when the power supply switch is turned on next time.

Specifically, when the power supply switch is turned on after the tip 5 is mounted next time on the distal end of the photometric unit 4 (while the tip 5 is being mounted on the distal end of the photometric unit 4), the information of the flag C is read from the third memory of the data storage unit 13 prior to the decision of step S105, and used in the decision of step S105.

Thus, even when the power supply switch is turned on with the used tip 5 being mounted on the distal end of the photometric unit 4, information (a warning or the like) obtained in the preceding measurement cycle with respect to a stain on the light-transmissive member 45 can be displayed.

The control process of the control means 10 of the component measuring device 1 in the stain detecting mode will be described below. The detailed stain detecting mode will not be described below.

As described above, when the power supply switch is turned on while the time setting/changing switch is being turned on, the component measuring device 1 is set to the stain detecting mode (step S301), as shown in FIG. 20. The test tip 20 is mounted on the distal end of the photometric unit 4 (step S302). When the calling switch is turned on (step S303), the light-emitting element 41 is energized once, and the stain detecting process described above is performed (step S304).

If no stain is confirmed, then it is determined that there is no stain, and a flag B indicative of no stain is set (B=1).

If no stain is not confirmed (the amount of light detected by the light-detecting element 42 is greater than the preset threshold), then it is determined there is a stain, and the flag B is not set (B=0).

The emission of light from the light-emitting element 41 in step S304 is not limited to one emission.

Then, it is determined whether the flag B=1 or not (step S305). If the flag B=1, then the liquid crystal display unit 9 displays "YES" indicating that there is no stain (step S306), after which control goes to a next process.

If the flag B=0, then the liquid crystal display unit 9 displays stain information representative of "NO" indicating that there is a stain (step S307), after which control goes to a next process.

With the component measuring device 1, as described above, since the passage in the holder 43 is closed by the light-transmissive member 45, dust, water, blood (specimen), or the like is reliably prevented from entering the passage in the holder 43 (the photometric unit 4). Therefore, the amount of a blood component in question can be measured with high measurement accuracy.

Inasmuch as a stain on the light-transmissive member 45 is detected according to the black level checking process, a stain on the light-transmissive member 45 can be detected highly accurately. Thus, measurements while the light-transmissive member 45 is being stained are prevented from occurring, and the measurement accuracy is further increased.

In the fourth embodiment, a holder member 47 may be incorporated as in the second embodiment and the third embodiment described above (the second embodiment and the third embodiment may be applied).

Though the component measuring device according to the present invention has been described above based on the illustrated embodiments, the present invention is not limited to the illustrated embodiments, and the structures of various parts may be replaced with any desired structures having the same functions. Furthermore, other desired structures may be added.

The present invention may be a combination of two or more desired structures (features) of the above embodiments.

According to the present invention, the light-emitting element and the light-detecting element are not limited to one set, but may be employed in a plurality of sets. It is possible to provide a light-emitting element and a light-detecting element for detecting a stain in addition to a light-emitting element and a light-detecting element for measuring a component. However, it is preferable to use the same elements to measure a component and detect a stain because the effect that a stain has on the wavelength of light used is of importance in measuring a component.

In the above embodiments, the specimen includes blood. However, the specimen is not limited to blood, but may be a body fluid such as urine, lymph fluid, cerebrospinal fluid, saliva, or the like, or a dilute solution thereof, or a concentrated solution thereof.

The component to be measured (given component) is not limited to glucose (blood glucose level), but may be cholesterol, uric acid, creatinine, lactic acid, hemoglobin (occult blood), various alcohols, various sugars, various protein, various vitamins, and various inorganic ions such as sodium.

In the above embodiments, an amount of a given component is measured. According to the present invention, however, a property of a given component may be measured, or both an amount and a property of a given component may be measured.

In the above embodiments, an O-ring (a sealing member made of an elastomeric material) is used as a representative sealing member. However, the sealing member may be made of any of various sealing materials (e.g., an adhesive) such as resin materials.

The component measuring devices according to the above embodiments are used in combination with a mounted tip having a test strip. The component measuring device according to the present embodiment may employ a tip in the form of a stick, a sheet, or any of other structures (forms).

INDUSTRIAL APPLICABILITY

According to the present invention, since dust, the specimen, or the like is prevented from entering into the passage in the photometric unit (into the photometric unit), an amount of a blood component in question can be measured with high measurement accuracy. Even if dust, the specimen, or the like is applied to the end of the photometric unit or the like, it can easily and reliably be removed.

According to the present invention, furthermore, a stain on the light-transmissive member can be detected with high accuracy. Since an amount of a blood component in question is prevented from being measured while the light-transmissive member is being stained, the measurement accuracy is increased. Since the component measuring device has the light-transmissive member, dust, the specimen, or the like is reliably prevented from entering into the passage in the photometric unit (into the photometric unit), so that an amount of a blood component in question can be measured with high measurement accuracy.

Therefore, the present invention has industrial applicability.

The invention claimed is:

1. A component measuring device for measuring at least one of a quantity or a property of a given component in a specimen by colorimetrically measuring a test member, comprising:
a tip mount for removably mounting a tip having the test member;
a photometric unit having a light-emitting element for applying light to said test member of said tip for measurement, a light-detecting element for detecting light reflected by said test member, and a holder in which is accommodated said light-emitting element and said light-detecting element;
a light-shielding test tip for being removably mounted on said tip mount,
wherein said holder has a passage for passing said light and said reflected light therethrough, and a light-transmissive member is disposed in a portion of said holder which is adapted to face said test member; and
stain detecting means for detecting a stain on said light-transmissive member based on an amount of light detected by said light-detecting element when light is emitted from said light-emitting element while said test tip is mounted on said tip mount,
wherein said stain detecting means is arranged to determine that there is a stain on said light-transmissive member if an amount of light detected by said light-detecting element is greater than a threshold.

2. The component measuring device according to claim 1, wherein said test tip has a lid-like member for covering a distal end of said tip mount.

3. The component measuring device according to claim 2, wherein at least said lid-like member of said test tip is black or dark in color.

4. The component measuring device according to claim 2, wherein the distance from the distal end of said tip mount to an inner wall of said lid-like member at a distal end thereof is 10 mm or greater while said test tip is mounted on said tip mount.

5. A component measuring device for measuring at least one of a quantity or a property of a given component in a specimen by calorimetrically measuring a test member, comprising:
a photometric unit having a light-emitting element for applying light to said test member for measurement, and a light-detecting element for detecting light reflected from said test member,
wherein said photometric unit has a passage for passing said light and said reflected light therethrough, and a light-transmissive member is disposed in a portion of said photometric unit which is adapted to face said test member; and
stain detecting means for detecting a stain on said light-transmissive member based on an amount of light detected by said light-detecting element when light is emitted from said light-emitting element,
wherein said stain detecting means is arranged to determine that there is a stain on said light-transmissive member if the amount of light detected by said light-detecting element is greater than a threshold.

6. The component measuring device according to claim 1, wherein a stain on said light-transmissive member is detected while said tip is not mounted on said tip mount.

7. The component measuring device according to claim 1, wherein a stain on said light-transmissive member is detected when a power supply of the component measuring device is turned on.

8. The component measuring device according to claim 1, having a stain detecting mode for detecting a stain on said light-transmissive member.

9. The component measuring device according to claim 1, further comprising storage means for storing results from the stain detecting means, wherein a stain on said light-transmissive member is detected after measurement, and a detected result is stored in said storage means.

10. The component measuring device according to claim 9, wherein when a stain on said light-transmissive member is not detected, information stored in said storage means is used.

11. The component measuring device according to claim 9, wherein when the component measuring device is powered on with said tip mounted on said tip mount, a stain on said light-transmissive member is not detected and information stored in said storage means is used.

12. The component measuring device according to claim 1, further comprising indicating means for indicating a detected result produced in detecting a stain on said light-transmissive member.

13. The component measuring device according to claim 1, wherein said light-transmissive member closes said passage with a sealing member interposed therebetween.

14. The component measuring device according to claim 5, wherein a stain on said light-transmissive member is detected while said tip is not mounted on said tip mount.

15. The component measuring device according to claim 5, wherein a stain on said light-transmissive member is detected when a power supply of the component measuring device is turned on.

16. The component measuring device according to claim 5, having a stain detecting mode for detecting a stain on said light-transmissive member.

17. The component measuring device according to claim 5, further comprising storage means for storing results from the stain detecting means, wherein a stain on said light-transmissive member is detected after measurement, and a detected result is stored in said storage means.

18. The component measuring device according to claim 5, further comprising indicating means for indicating a detected result produced in detecting a stain on said light-transmissive member.

19. The component measuring device according to claim 5, wherein said light-transmissive member closes said passage with a sealing member interposed therebetween.

\* \* \* \* \*